US010523065B2

(12) United States Patent
Jin et al.

(10) Patent No.: US 10,523,065 B2
(45) Date of Patent: Dec. 31, 2019

(54) ULTRASOUND PROBE AND CHARGING METHOD THEREOF

(71) Applicant: SAMSUNG MEDISON CO., LTD., Hongcheon-gun (KR)

(72) Inventors: Gil-ju Jin, Hongcheon-gun (KR); Ho-san Han, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 213 days.

(21) Appl. No.: 15/193,648

(22) Filed: Jun. 27, 2016

(65) Prior Publication Data
US 2017/0179774 A1   Jun. 22, 2017

(30) Foreign Application Priority Data
Dec. 16, 2015 (KR) ........................ 10-2015-0180195

(51) Int. Cl.
| | | |
|---|---|---|
| *H02J 50/80* | (2016.01) | |
| *H02J 50/90* | (2016.01) | |
| *H02J 50/12* | (2016.01) | |
| *A61B 8/00* | (2006.01) | |
| *H02J 7/02* | (2016.01) | |
| *G01S 7/52* | (2006.01) | |

(52) U.S. Cl.
CPC ............ *H02J 50/90* (2016.02); *A61B 8/4245* (2013.01); *A61B 8/4438* (2013.01); *A61B 8/4472* (2013.01); *A61B 8/56* (2013.01); *G01S 7/52096* (2013.01); *H02J 7/025* (2013.01); *H02J 7/027* (2013.01); *H02J 50/12* (2016.02); *H02J 50/80* (2016.02)

(58) Field of Classification Search
CPC ............. H02J 50/00; H02J 50/80; H04B 5/00
USPC ................................... 307/104, 154
See application file for complete search history.

(56) References Cited

U.S. PATENT DOCUMENTS

| | | | |
|---|---|---|---|
| 6,967,462 B1 | 11/2005 | Landis | |
| 7,893,564 B2* | 2/2011 | Bennett | H02J 17/00 307/104 |
| 9,706,979 B2* | 7/2017 | Yamamoto | A61B 8/462 |
| 9,887,584 B1* | 2/2018 | Bell | H02J 17/00 |
| 9,901,324 B2* | 2/2018 | Cho | A61B 8/5207 |
| 9,912,379 B2* | 3/2018 | Hyde | H02J 50/80 |
| 9,923,386 B1* | 3/2018 | Leabman | H02J 5/005 |
| 2004/0142733 A1* | 7/2004 | Parise | B01F 5/0614 455/572 |
| 2005/0228281 A1* | 10/2005 | Nefos | A61B 8/08 600/446 |

(Continued)

FOREIGN PATENT DOCUMENTS

| | | |
|---|---|---|
| CN | 104640178 A | 5/2015 |
| EP | 2 915 490 A1 | 9/2015 |

(Continued)

OTHER PUBLICATIONS

Communication dated Apr. 18, 2017 issued by the European Patent Office in counterpart European Patent Application No. 16188100.8.

*Primary Examiner* — Adi Amrany
(74) *Attorney, Agent, or Firm* — Sughrue Mion, PLLC

(57) ABSTRACT

Provided are a wireless ultrasound probe and a method of charging a battery included in the wireless ultrasound probe by receiving wireless power that is directionally transmitted toward a position of the wireless ultrasound probe and focusing received wireless power.

34 Claims, 19 Drawing Sheets

(56) References Cited

U.S. PATENT DOCUMENTS

| | | | | |
|---|---|---|---|---|
| 2008/0272962 A1* | 11/2008 | Milano | ............... | H01Q 1/007 342/374 |
| 2010/0168576 A1* | 7/2010 | Poland | ............... | A61B 8/00 600/443 |
| 2010/0185096 A1 | 7/2010 | Miyachi et al. | | |
| 2010/0315045 A1* | 12/2010 | Zeine | ............... | H02J 7/025 320/137 |
| 2012/0197124 A1* | 8/2012 | Nakamura | ............... | A61B 8/42 600/443 |
| 2012/0226160 A1* | 9/2012 | Kudoh | ............... | A61B 8/13 600/443 |
| 2012/0235499 A1* | 9/2012 | Liu | ............... | H02J 17/00 307/104 |
| 2013/0053697 A1* | 2/2013 | Holl | ............... | A61B 8/54 600/459 |
| 2013/0069587 A1 | 3/2013 | Kuk | | |
| 2013/0241468 A1 | 9/2013 | Moshfeghi | | |
| 2014/0323861 A1 | 10/2014 | Jin et al. | | |
| 2014/0323869 A1* | 10/2014 | Jin | ............... | A61B 8/565 600/459 |
| 2014/0371592 A1* | 12/2014 | Yamamoto | ............... | A61B 8/14 600/443 |
| 2015/0042266 A1* | 2/2015 | Chen | ............... | H02J 7/0004 320/108 |
| 2015/0065882 A1* | 3/2015 | Cho | ............... | A61B 8/5207 600/443 |
| 2015/0260691 A1* | 9/2015 | Nakayama | ............... | G01N 29/2481 73/661 |
| 2016/0066893 A1* | 3/2016 | Cho | ............... | A61B 8/54 600/459 |
| 2016/0135791 A1* | 5/2016 | Park | ............... | A61B 8/54 600/459 |
| 2016/0174937 A1* | 6/2016 | Bakshi | ............... | A61B 8/4472 600/459 |
| 2017/0105703 A1* | 4/2017 | Han | ............... | A61B 8/565 |
| 2017/0354396 A1* | 12/2017 | Lee | ............... | A61B 8/4472 |

FOREIGN PATENT DOCUMENTS

| | | |
|---|---|---|
| KR | 10-2012-0068581 A | 6/2012 |
| KR | 10-2013-0127228 A | 11/2013 |
| WO | 2016018867 A1 | 2/2016 |

* cited by examiner

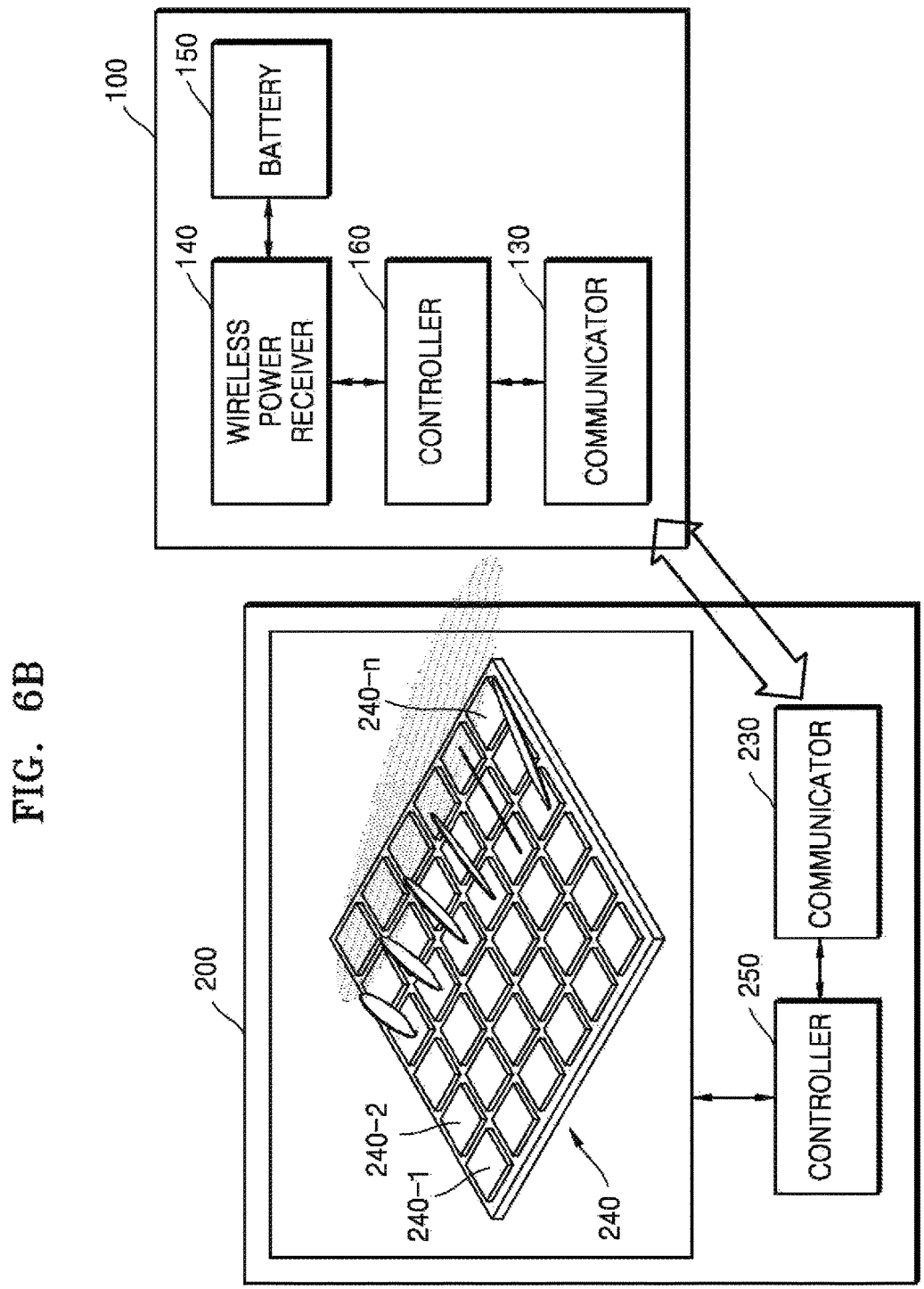

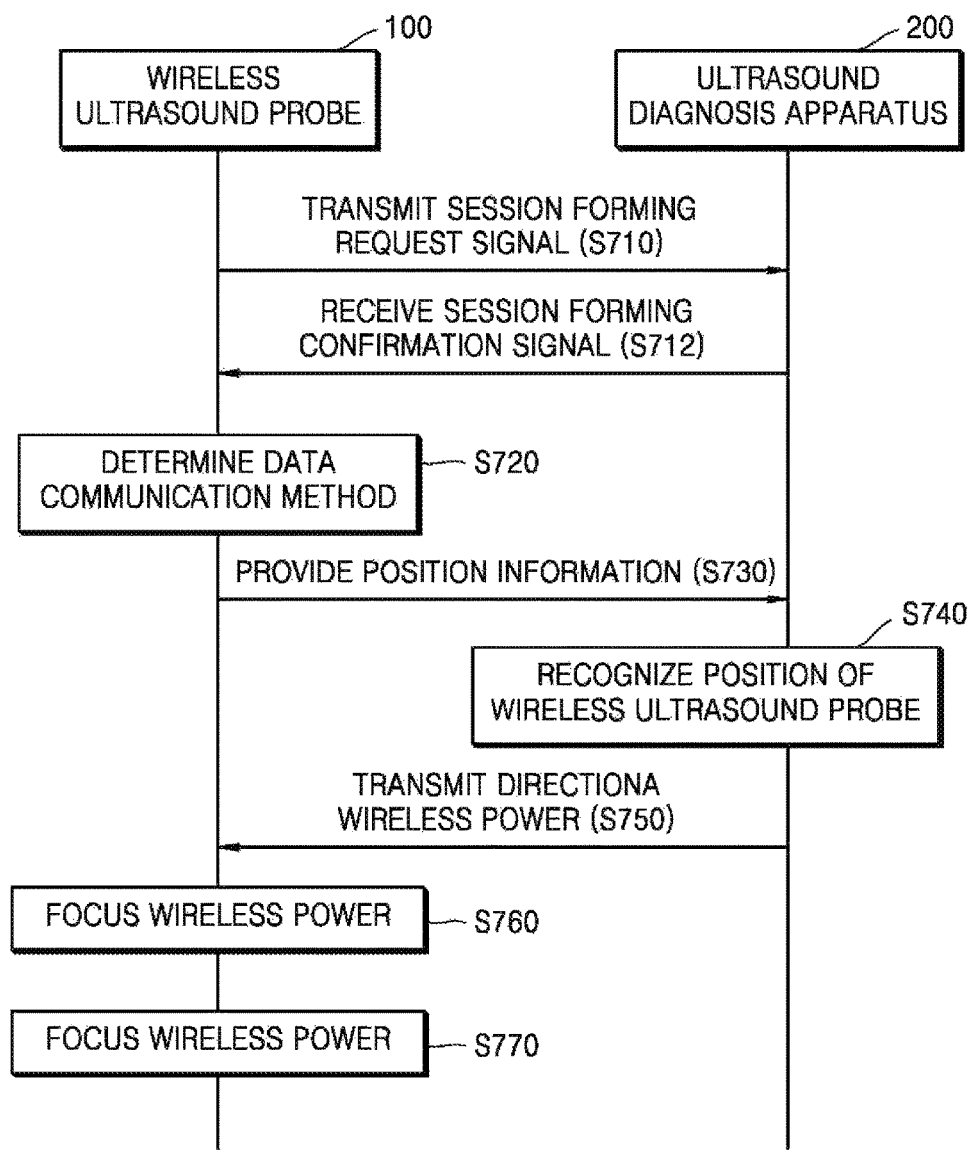

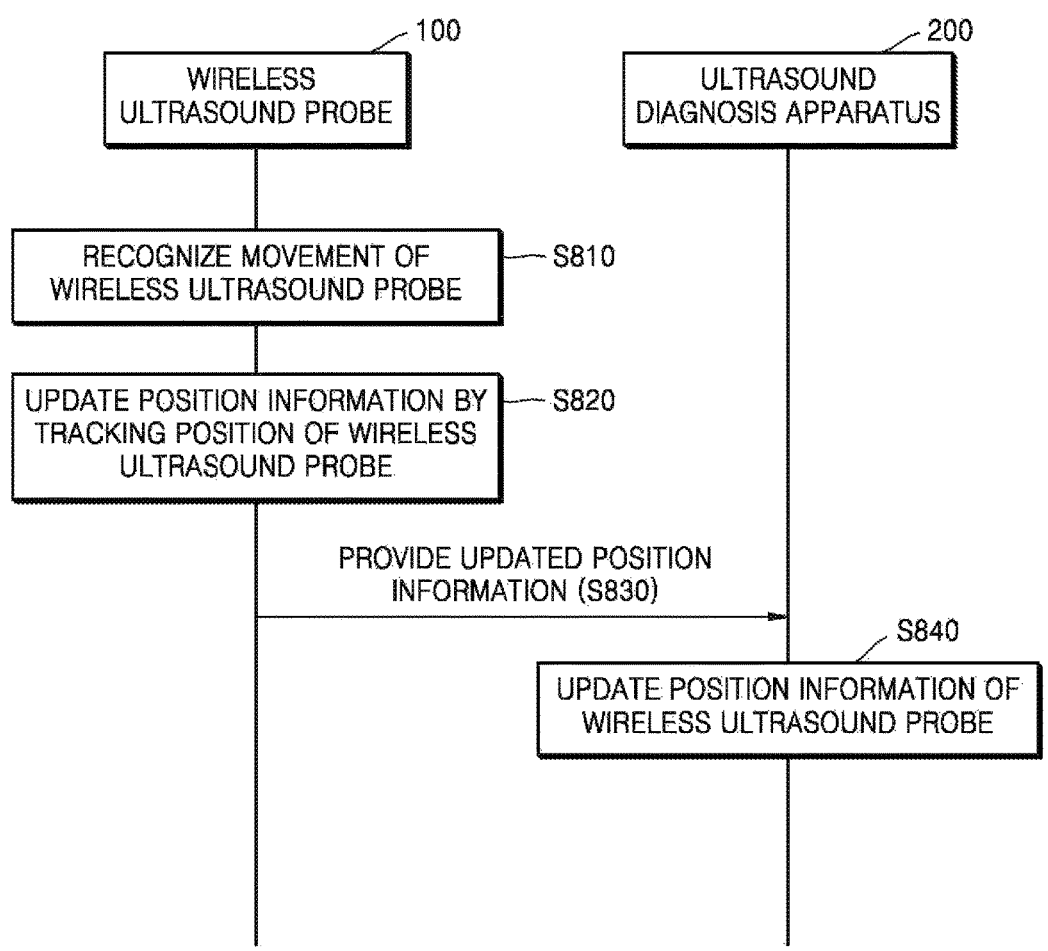

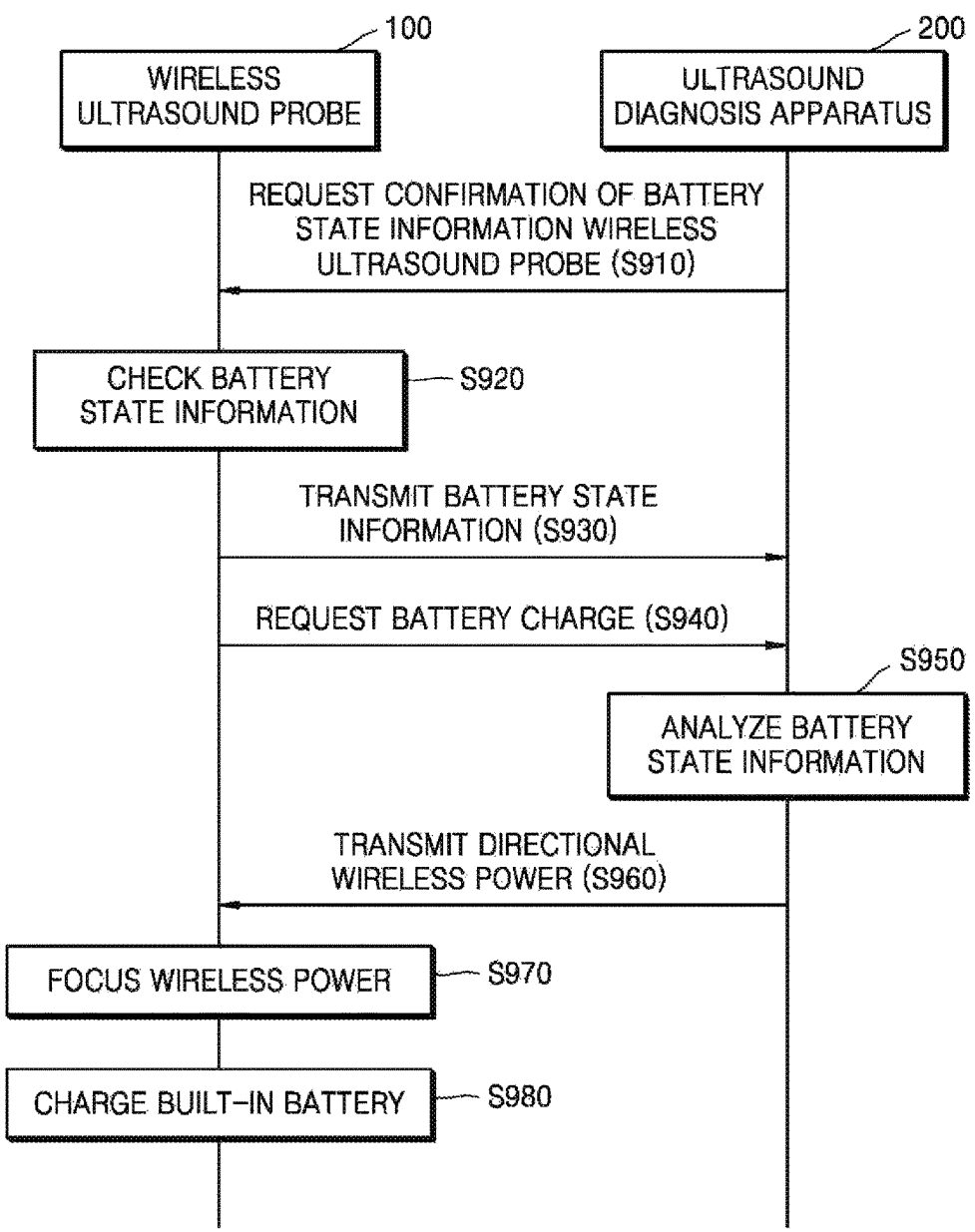

ULTRASOUND PROBE AND CHARGING METHOD THEREOF

CROSS-REFERENCE TO RELATED APPLICATION

This application claims the benefit of Korean Patent Application No. 10-2015-0180195, filed on Dec. 16, 2015, in the Korean Intellectual Property Office, the disclosure of which is incorporated herein in its entirety by reference.

BACKGROUND

1. Field

One or more embodiments relate to an ultrasound probe and a method of charging the ultrasound probe, and more particularly, to a wireless ultrasound probe in which a battery is charged by receiving wireless power from an ultrasound diagnosis apparatus or other apparatuses, and a method of charging the wireless ultrasound probe.

2. Description of the Related Art

Ultrasound systems are used to obtain an image of a certain inner portion of an object by irradiating an ultrasound signal generated by a transducer of an ultrasound probe toward the portion and receiving information about an echo signal reflected from the portion. Particularly, the ultrasound system is used for medical purposes, such as observation of the inside of the object, detection of foreign materials, assessment of an injury, imaging of characteristics, etc.

The ultrasound system has high stability, is capable of displaying an image in real time, and is safe due to there being no radioactive exposure compared to a diagnosis apparatus using an X-ray. Accordingly, the ultrasound system exhibiting the above merits has been widely used solely or with other medical diagnosis apparatuses. When obtaining an ultrasound image of the object using an ultrasound probe, a user is often inconvenienced by a communication cable connecting the ultrasound probe to a diagnosis apparatus.

Recently, in order to improve operability of an ultrasound probe by removing the communication cable or addressing the inconvenience due to the communication cable, a wireless ultrasound probe that connects the ultrasound diagnosis apparatus via wireless communication has been developed. However, the wireless ultrasound probe has a problem in that a usage time of the wireless ultrasound probe is limited by the energy consumption of a built-in battery. According to recent technology, in which a transmission efficiency of wireless power is not high, transmission power needs to be increased according to a necessary power standard to secure convenience in using a wireless ultrasound probe. Furthermore, when power is wirelessly supplied to the ultrasound probe used in close contact with a patient, a human body transmissive type wireless power transmission method may have a direct influence on the body of the patient. Accordingly, there is a demand for a human body transmissive type wireless power transmission method having high reliability and stability, which is harmless to a human body and does not affect other apparatuses.

SUMMARY

One or more embodiments include a wireless ultrasound probe in which wireless power is directionally transmitted toward a position of the wireless ultrasound probe and a battery of the wireless ultrasound probe is charged by receiving the transmitted wireless power, thereby improving a battery charging efficiency, and a method of charging the wireless ultrasound probe.

Additional aspects will be set forth in part in the description which follows and, in part, will be apparent from the description, or may be learned by practice of the presented embodiments.

According to one or more embodiments, a method of charging a wireless ultrasound probe wirelessly connected to an ultrasound diagnosis apparatus includes providing a position information of the wireless ultrasound probe, obtained through data communication for transmitting ultrasound image data obtained from an object to the ultrasound diagnosis apparatus, and charging a battery included in the wireless ultrasound probe by focusing wireless power directionally transmitted by the ultrasound diagnosis apparatus according to the position information.

The data communication may be short-distance communication capable of tracking the position of the wireless ultrasound probe.

The data communication may include at least one of short-distance data communication methods including 60 GHz millimeter wave (mmWave), wireless local area network (LAN), Wi-Fi, Bluetooth, Zigbee, Wi-Fi direct (WFD), ultra wideband (UWB), infrared data association (IrDA), Bluetooth low energy (BLE), near field communication (NFC), wireless broadband Internet (Wibro), world interoperability for microwave access (WiMAX), shared wireless access protocol (SWAP), wireless gigabit alliance (WiGig), and radio frequency (RF) communications.

The providing of the position information of the wireless ultrasound probe to the ultrasound diagnosis apparatus may include determining any one of at least one short-distance communication method for obtaining the position information of the wireless ultrasound probe.

The providing of the position information of the wireless ultrasound probe to the ultrasound diagnosis apparatus may include updating the position information of the wireless ultrasound probe according to a movement of a user using the wireless ultrasound probe, and providing the updated position information to the ultrasound diagnosis apparatus.

The charging of the battery may include charging the battery by focusing the wireless power transmitted by the ultrasound diagnosis apparatus by using a magnetic resonance method.

The charging of the battery may include charging the battery by focusing the wireless power transmitted by the ultrasound diagnosis apparatus by using a directional beam-focusing method.

The method may further include transmitting raw data to the ultrasound diagnosis apparatus, the raw data being obtained by transmitting an ultrasound signal to the object and receiving an echo signal reflected from the object.

The method may further include providing at least one of information about setting of the wireless ultrasound probe including information about identification of the wireless ultrasound probe, ultrasound preset setting information, information about a user of the wireless ultrasound probe, and information about the object, to the ultrasound diagnosis apparatus.

The method may further include checking information about a state of the battery including a remaining amount of charge of the battery, a usage time of the battery, and a use state of the battery included in the wireless ultrasound probe, and requesting transmission of wireless power from the ultrasound diagnosis apparatus based on the information about the state of the battery.

The checking of the information about the state of the battery may include providing an alarm signal to a user when the remaining amount of charge of the battery is less than a predetermined value.

The requesting of the transmission of wireless power may include requesting transmission of wireless power from the ultrasound diagnosis apparatus only when the wireless ultrasound probe is not in use.

The method may further include displaying a transmission type of wireless power received from the ultrasound diagnosis apparatus.

The method may further include dividing a capacity of the battery into a first battery capacity and a second battery capacity, and primarily discharging the first battery capacity while the wireless ultrasound probe is in use.

According to one or more embodiments, a wireless ultrasound probe wirelessly connected to an ultrasound diagnosis apparatus includes an ultrasound transceiver transmitting an ultrasound signal to an object and receiving an echo signal reflected from the object, a communicator transmitting ultrasound image data obtained from the echo signal to the ultrasound diagnosis apparatus, a controller identifying a position information of the wireless ultrasound probe through data communication via which the communicator transmits the ultrasound image data to the ultrasound diagnosis apparatus, and controlling the communicator to provide the position information of the wireless ultrasound probe to the ultrasound diagnosis apparatus, and a wireless power receiver charging a battery included in the wireless ultrasound probe by focusing wireless power directionally transmitted by the ultrasound diagnosis apparatus according to the position information.

The controller may control the communicator to perform data communication with the ultrasound diagnosis apparatus by using short-distance communication to track a position of the wireless ultrasound probe.

The communicator may use at least one of short-distance data communication methods including 60 GHz millimeter wave (mmWave), wireless local area network (LAN), Wi-Fi, Bluetooth, Zigbee, Wi-Fi direct (WFD), ultra wideband (UWB), infrared data association (IrDA), Bluetooth low energy (BLE), near field communication (NFC), wireless broadband Internet (Wibro), world interoperability for microwave access (WiMAX), shared wireless access protocol (SWAP), wireless gigabit alliance (WiGig), and radio frequency (RF) communications, and the controller may identify the position information of the wireless ultrasound probe by using at least one of the short-distance data communication methods.

The controller may determine any one of at least one short-distance communication method for obtaining the position information of the wireless ultrasound probe.

The controller may update the position information of the wireless ultrasound probe according to a movement of a user using the wireless ultrasound probe, and the communicator may transmit the updated position information to the ultrasound diagnosis apparatus.

The wireless power receiver may charge the battery by focusing the wireless power transmitted by the ultrasound diagnosis apparatus by using a magnetic resonance method.

The wireless power receiver may charge the battery by focusing the wireless power transmitted by the ultrasound diagnosis apparatus by using a directional beamfocusing method.

The communicator may transmit raw data obtained from the echo signal to the ultrasound diagnosis apparatus.

The communicator may transmit at least one of information about setting of the wireless ultrasound probe including information about identification of the wireless ultrasound probe, ultrasound preset setting information, information about a user of the wireless ultrasound probe, and information about the object, to the ultrasound diagnosis apparatus.

The controller may check information about a state of the battery including a remaining amount of charge of the battery, a usage time of the battery, and a use state of the battery, and requests transmission of wireless power from the ultrasound diagnosis apparatus based on the information about the state of the battery.

The wireless ultrasound probe may further include an alarm display unit that provides an alarm signal to a user when the remaining amount of charge of the battery is less than a predetermined value.

The controller may request transmission of wireless power from the ultrasound diagnosis apparatus only when the wireless ultrasound probe is not in use.

The wireless ultrasound probe may further include a display that displays a transmission type of wireless power received from the ultrasound diagnosis apparatus The controller may divide a capacity of the battery into a first battery capacity and a second battery capacity and primarily discharges the first battery capacity while the wireless ultrasound probe is in use.

According to one or more embodiments, an ultrasound system includes an ultrasound probe obtaining ultrasound image data by transmitting an ultrasound signal to an object and receiving an echo signal reflected from the object, and an ultrasound diagnosis apparatus wirelessly connected to the ultrasound probe and wirelessly transmitting power to the ultrasound probe, in which the ultrasound probe identifies position information of the wireless ultrasound probe through data communication for transceiving the ultrasound image data with respect to the ultrasound diagnosis apparatus, and the ultrasound diagnosis apparatus charges a battery included in the wireless ultrasound probe by directionally transmitting wireless power to the wireless ultrasound probe based on the position information of the ultrasound probe.

The ultrasound diagnosis apparatus may include a wireless power transmitter that directionally transmits the wireless power toward the position of the ultrasound probe by controlling a delay time of a wireless power signal in a particular order.

The ultrasound diagnosis apparatus may further include a direction controller that is connected to the wireless power transmitter and changes a transmission direction of the wireless power transmitter to at least one of a first direction, a second direction perpendicular to the first direction, and a third direction perpendicular to each of the first direction and the second direction.

The direction controller may rotate the transmission direction of the wireless power transmitter to at least one of the first direction, the second direction, and the third direction.

According to one or more embodiments, a non-transitory computer readable recording medium having recorded thereon a program, which when executed by a computer, performs the method of charging a wireless ultrasound probe wirelessly connected to an ultrasound diagnosis apparatus includes providing a position information of the wireless ultrasound probe, obtained through data communication for transmitting ultrasound image data obtained from an object to the ultrasound diagnosis apparatus, and charging a battery included in the wireless ultrasound probe by focusing wireless power directionally transmitted by the ultrasound diagnosis apparatus according to the position information.

BRIEF DESCRIPTION OF THE DRAWINGS

These and/or other aspects will become apparent and more readily appreciated from the following description of the embodiments, taken in conjunction with the accompanying drawings in which:

FIGS. 6A to 6C are conceptual views for explaining a method of receiving directional wireless power, which is performed by a wireless ultrasound probe, according to an embodiment;

FIG. 7 is a flowchart of a method of charging a battery by receiving directional wireless power from an ultrasound diagnosis apparatus, which is performed by a wireless ultrasound probe, according to an embodiment;

FIG. 8 is a flowchart of a method of providing position information to an ultrasound diagnosis apparatus, which is performed by a wireless ultrasound probe, according to an embodiment;

FIG. 9 is a flowchart of a method of charging a battery of a wireless ultrasound probe by receiving directional wireless power from an ultrasound diagnosis apparatus based on information about a state of the battery, according to an embodiment;

DETAILED DESCRIPTION

Figure 1:
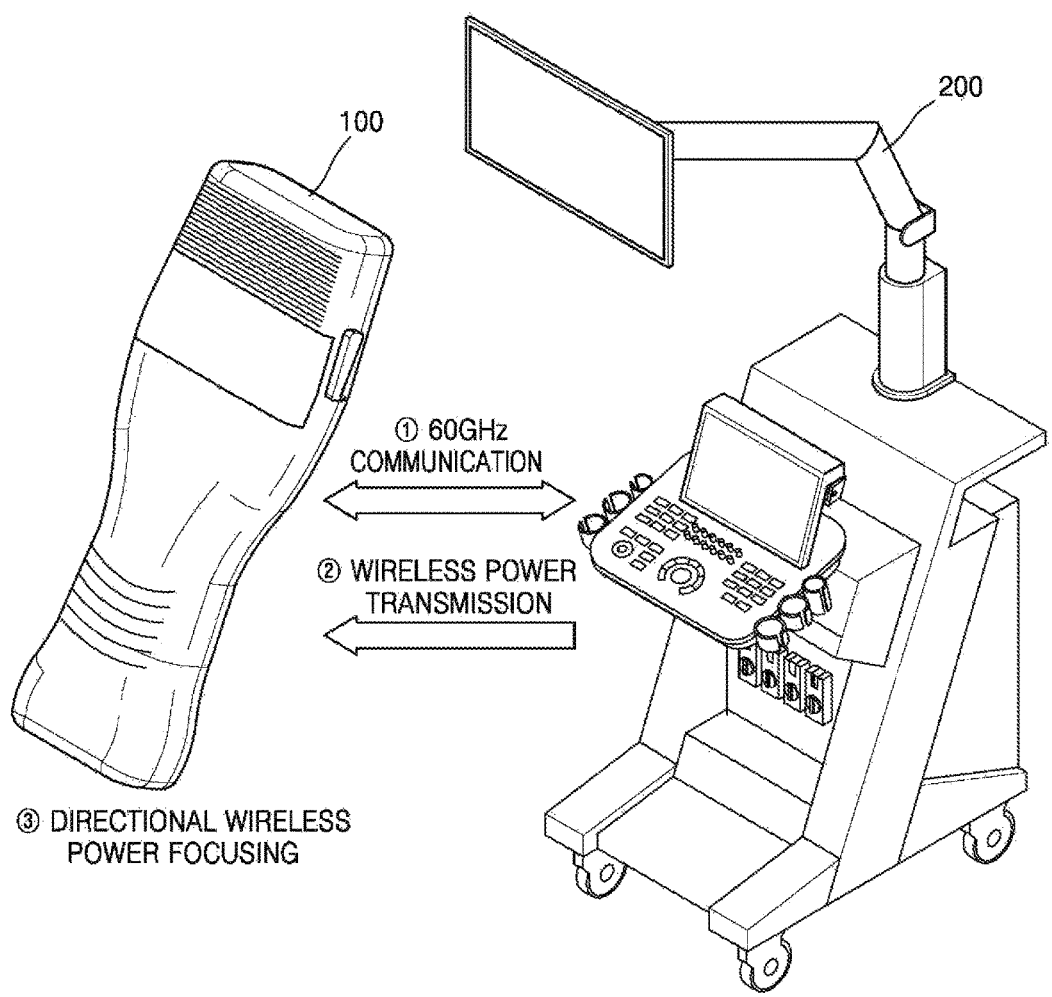
FIG. 1 is a conceptual view for explaining a method of charging a wireless ultrasound probe, according to an embodiment.

Advantages and features of one or more embodiments of the present inventive concept and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present inventive concept will only be defined by the appended claims.

Hereinafter, the terms used in the specification will be briefly described, and then the present inventive concept will be described in detail.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the inventive concept.

When a part "includes" or "comprises" an element, unless there is a particular description contrary thereto, the part can further include other elements, not excluding the other elements. Terms such as "~ unit" stated in the specification may signify software, or a hardware element such as a field-programmable gate array (FPGA) or an application-specific integrated circuit (ASIC), and the "~ unit" performs a certain function or operation. However, the term "unit" is not limited to software or hardware. The "unit" may be formed so as to be in an addressable storage medium, or may be formed so as to operate one or more processors. Accordingly, the unit as an example includes constituent elements such as software constituent elements, object-oriented software constituent elements, class constituent elements, and task constituent elements, processes, functions, attributes, procedures, sub-routines, segments of program codes, drivers, firmware, microcodes, circuits, data, databases, data structures, tables, arrays, and variables. The constituent elements and functions provided by the "units" may be combined into a smaller number of constituent elements and units or may be further divided into additional constituent elements and units.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Furthermore, in the present specification, terms such as "first" and "second" are used herein merely to describe a variety of members, parts, areas, layers, and/or portions, but the constituent elements are not limited by the terms. It is obvious that the members, parts, areas, layers, and/or portions are not limited by the terms. Accordingly, the terms such as "first" and "second" do not indicate an order or priority between constituent elements.

Hereinafter, the present inventive concept will be described in detail by explaining embodiments of the inventive concept with reference to the attached drawings. In the description of the present inventive concept, certain detailed explanations of the related art are omitted when it is deemed that they may unnecessarily obscure the essence of the inventive concept.

FIG. 1 is a conceptual view for explaining a method of charging a wireless ultrasound probe 100, according to an embodiment.

Referring to FIG. 1, the wireless ultrasound probe 100 may be connected to an ultrasound diagnosis apparatus 200 via a wireless communication method and may receive wireless power from the ultrasound diagnosis apparatus 200. The wireless ultrasound probe 100 and the ultrasound diagnosis apparatus 200 may embody an ultrasound system.

The wireless ultrasound probe 100 may transmit an ultrasound signal to an object and receive an echo signal reflected from the object, forming a received signal. The wireless ultrasound probe 100 may perform image processing on the received signal to generate ultrasound image data. The wireless ultrasound probe 100 may transmit generated ultrasound image data to the ultrasound diagnosis apparatus 200. The wireless ultrasound probe 100 may be wirelessly connected to the ultrasound diagnosis apparatus 200 via a wireless communication method.

The ultrasound diagnosis apparatus 200 may be wirelessly connected to the wireless ultrasound probe 100 and may display an ultrasound image by using the ultrasound image data received from the wireless ultrasound probe 100. For example, the ultrasound diagnosis apparatus 200 may represent not only an ultrasound image of a gray scale obtained by scanning the object according to an A mode (amplitude mode), a B mode (brightness mode), and an M mode (motion mode), but also a movement of the object, as a Doppler image. In an embodiment, the ultrasound diagnosis apparatus 200 may be embodied not only as a cart type but also as a portable type. A portable ultrasound diagnosis apparatus may include a picture archiving and communication system (PACS) viewer, hand-carried cardiac ultrasound (HCU) equipment, smart phones, laptop computers, personal digital assistants (PDAs), tablet personal computers (PCs), etc., but not limited thereto.

In an embodiment, the ultrasound diagnosis apparatus 200 may be an apparatus for generating an ultrasound image by processing the ultrasound image data received from the wireless ultrasound probe 100 and displaying a generated image, or an apparatus that simply embodies only an image display function without a separate image processing function. In other words, the ultrasound diagnosis apparatus 200 may include a display apparatus that receives an image from the wireless ultrasound probe 100 and displays the received image on a screen without additional processing.

The wireless ultrasound probe 100 may be wirelessly connected to the ultrasound diagnosis apparatus 200 by a data communication method. In an embodiment, the wireless ultrasound probe 100 may be wirelessly connected to the ultrasound diagnosis apparatus 200 by a 60 GHz millimeter wave (mm Wave) short-distance wireless communication method. However, the present disclosure is not limited thereto, and the wireless ultrasound probe 100 may be connected to the ultrasound diagnosis apparatus 200 by using at least one of data communication methods, for example, wireless local area network (LAN), Wi-Fi, Bluetooth, Zigbee, Wi-Fi direct (WFD), ultra wideband (UWB), infrared data association (IrDA), Bluetooth low energy (BLE), near field communication (NFC), wireless broadband Internet (Wibro), world interoperability for microwave access (WiMAX), shared wireless access protocol (SWAP), wireless gigabit alliance (WiGig), and radio frequency (RF) communications.

The wireless ultrasound probe 100 may transmit information about a position of the wireless ultrasound probe 100 to the ultrasound diagnosis apparatus 200 by a data communication method. In an embodiment, the wireless ultrasound probe 100 may track the position of the wireless ultrasound probe 100 that changes according to a use of the wireless ultrasound probe 100, by a short-distance communication method. In an embodiment, the wireless ultrasound probe 100 may transmit information about the position of the wireless ultrasound probe 100 to the ultrasound diagnosis apparatus 200 by the 60 GHz millimeter wave short-distance wireless communication method.

The wireless ultrasound probe 100 may receive wireless power that is directionally transmitted by the ultrasound diagnosis apparatus 200. In an embodiment, the ultrasound diagnosis apparatus 200 may directionally transmit wireless power based on the information about the position of the wireless ultrasound probe 100 by the 60 GHz millimeter wave) short-distance wireless communication method. In an embodiment, the ultrasound diagnosis apparatus 200 may transmit wireless power to the wireless ultrasound probe 100 in a directional beam focusing method by using a wireless power transmission module including a retrodirective beam-forming antenna. In an embodiment, the ultrasound diagnosis apparatus 200 may transmit wireless power to the wireless ultrasound probe 100 by a magnetic resonance method.

The wireless ultrasound probe 100 may charge a built-in battery in the wireless ultrasound probe 100 by focusing the wireless power that is directionally transmitted. In an embodiment, the wireless ultrasound probe 100 may charge the battery of the wireless ultrasound probe 100 by focusing a directional magnetic field.

The wireless ultrasound probe 100 according to an embodiment may provide the information about the position of the wireless ultrasound probe 100 by a data communication method to wirelessly connect the ultrasound diagnosis apparatus 200, and may charge the battery by focusing the wireless power that is directionally transmitted based on the information about the position of the wireless ultrasound probe 100. According to a method of charging the wireless ultrasound probe 100 according to the present embodiment, the position of the wireless ultrasound probe 100 may be identified by the data communication method between the wireless ultrasound probe 100 and the ultrasound diagnosis apparatus 200, thereby obtaining general purpose characteristics. Furthermore, according to the present embodiment, as wireless power is directionally transmitted based on the position of the wireless ultrasound probe 100, an energy transmission efficiency and an efficiency of charging the wireless ultrasound probe 100 may be improved. Thus, a method of charging the wireless ultrasound probe 100 which reduces a magnetic field that transmits through a body of a patient or a user using the wireless ultrasound probe 100 and/or the ultrasound diagnosis apparatus 200, and the wireless ultrasound probe 100, may be provided.

Figure 2:
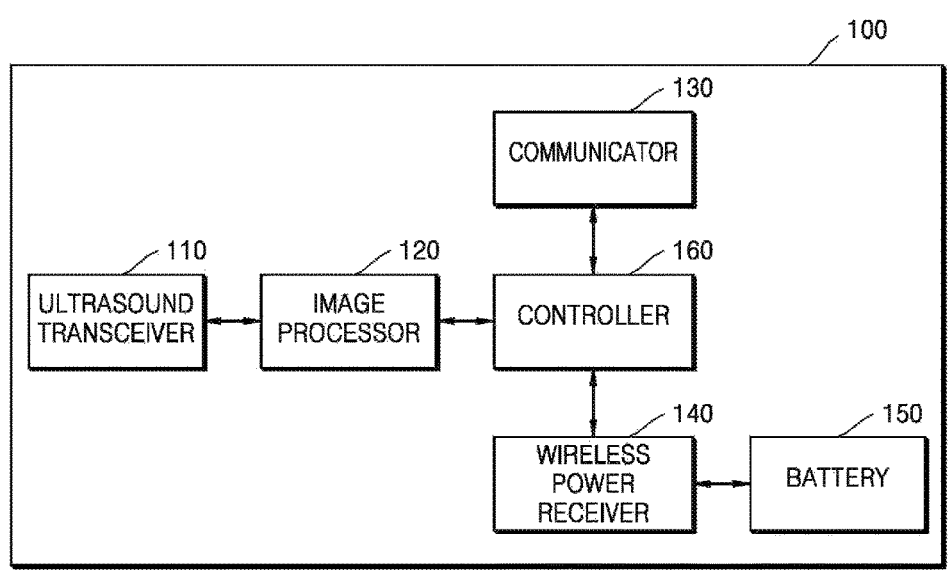
FIG. 2 is a block diagram illustrating a structure of a wireless ultrasound probe according to an embodiment.

FIG. 2 is a block diagram illustrating a structure of the wireless ultrasound probe 100 according to the present embodiment.

Referring to FIG. 2, the wireless ultrasound probe 100 may include an ultrasound transceiver 110, an image processor 120, a communicator 130, a wireless power receiver 140, a battery 150, and a controller 160.

The ultrasound transceiver 110 transmits an ultrasound signal to the object and receives an echo signal reflected from the object. The ultrasound transceiver 110 may generate a pulse for forming a transmissive ultrasound wave according to a certain pulse repetition frequency (PRF). The ultrasound transceiver 110 may apply a delay time to determine transmission directionality to the pulse. Each pulse to which the delay time is applied may correspond to each of a plurality of piezoelectric vibrators included in a transducer. The ultrasound transceiver 110 may transmit an ultrasound signal to the object by applying the pulse corresponding to each of the piezoelectric vibrators at a timing corresponding to each pulse to which the delay time is applied.

The image processor 120 may generate ultrasound image data corresponding to a data type determined by the controller 160 from the echo signal received from the ultrasound transceiver 110. The image processor 120 may generate ultrasound image data by processing the echo signal reflected from the object. The image processor 120 may amplify the echo signal for each channel and perform analog-digital (AD) conversion on an amplified echo signal. The image processor 120 may apply the delay time to determine receiving directionality to a digitally converted echo signal.

The communicator 130 transmits the ultrasound image data generated by the image processor 120 to the ultrasound diagnosis apparatus 200 (see FIG. 1). In an embodiment, the communicator 130 may transmit raw data generated by performing analog-digital conversion on the echo signal amplified by the image processor 120 to the ultrasound diagnosis apparatus 200. In an embodiment, the communicator 130 may transmit at least one piece of information about setting of the wireless ultrasound probe 100 including information about identification of the wireless ultrasound probe 100, ultrasound preset setting information, information about a user of the wireless ultrasound probe 100, and information about an object, to the ultrasound diagnosis apparatus 200.

The communicator 130 may perform wireless communication with the ultrasound diagnosis apparatus 200. The communicator 130 may perform data communication with the ultrasound diagnosis apparatus 200 by at least one of short-distance communication methods including, for example, LAN, Wi-Fi, Bluetooth, Zigbee, WFD, UWB, IrDA, BLE, NFC, Wibro, WiMAX, SWAP, WiGig, and RF communications. In an embodiment, the communicator 130 may perform data communication with the ultrasound diagnosis apparatus 200 by the 60 GHz millimeter wave short-distance wireless communication method.

The communicator 130 may transmit the information about the position of the wireless ultrasound probe 100 to the ultrasound diagnosis apparatus 200 under the control of the controller 160.

In an embodiment, the communicator 130 may communicate with an external device or server by being connected to a network in a wired or wireless manner. The communicator 130 may exchange data with a hospital server or another medical apparatus in a hospital, which is connected thereto via a PACS. Furthermore, the communicator 130 may perform data communication according to the digital imaging and communications in medicine (DICOM) standard.

The communicator 130 may transmit or receive data related to diagnosis of the object, e.g., an ultrasound image, ultrasound data, and Doppler data of the object, via the network and may also transmit or receive medical images captured by another medical apparatus, e.g., a computed tomography (CT) apparatus, a magnetic resonance imaging (MRI) apparatus, or an X-ray apparatus. Furthermore, the communicator 130 may receive information about a diagnosis history or medical treatment schedule of a patient from a server and utilizes the received information to diagnose the patient. Furthermore, the communicator 130 may perform data communication not only with a server or a medical apparatus in a hospital, but also with a portable terminal of a medical doctor or patient.

The wireless power receiver 140 receives the wireless power that is directionally transmitted by the ultrasound diagnosis apparatus 200, and charges the battery 150 by focusing received wireless power. In an embodiment, the wireless power receiver 140 may receive wireless power in the form of a magnetic field beam that is directionally transmitted by a wireless power transmitter 240 (see FIGS. 6A to 6C) including a retrodirective antenna. In an embodiment, the wireless power receiver 140 may charge the battery 150 by focusing wireless power transmitted by the magnetic resonance method. In an embodiment, the wireless power receiver 140 may charge the battery 150 by focusing wireless power transmitted in a dipole coil resonant system (DCRS).

The battery 150 supplies power needed to operate the wireless ultrasound probe 100. The battery 150 may be charged by receiving the wireless power focused by the wireless power receiver 140. The battery 150 may include, for example, at least one of lithium-ion (Li-ion), nickelmetal hydride (Ni-MH), lead oxide (PbOx), and sodium-sulfur (Na—S). However, the present disclosure is not limited thereto and the battery 150 may include a material capable of charging, such as, lithium metal oxide, an organic electrode material, and transition metal.

The controller 160 determines a data communication method used for transmitting the ultrasound image data generated by the image processor 120 to the ultrasound diagnosis apparatus 200, identifies information about the position of the wireless ultrasound probe 100 based on a determined data communication method, and controls the communicator 130 to provide the information about the position of the wireless ultrasound probe 100 to the ultrasound diagnosis apparatus 200.

The controller 160 may determine at least one of a wireless communication method, a usable bandwidth, a transmission speed for a communication channel, a communication channel type, and an identifier, which are used by the ultrasound diagnosis apparatus 200, based on information about the ultrasound diagnosis apparatus 200.

In an embodiment, the controller 160 may select at least one image processing operation of a plurality of sequential image processing operations to be performed to generate a displayable ultrasound image from the echo signal, based on the type of determined data. In an embodiment, the controller 160 may obtain the information about the ultrasound diagnosis apparatus 200 through the communicator 130. The controller 160 may determine the type of data configured to be processed by the ultrasound diagnosis apparatus 200, based on the information about the ultrasound diagnosis apparatus 200, and may determine a method of performing data communication with the ultrasound diagnosis apparatus 200. For example, when raw data that is generated as the image processor 120 performs AD conversion on the echo signal reflected from the object is transmitted to the ultrasound diagnosis apparatus 200, the controller 160 may control the communicator 130 to use a 60 GHz millimeter wave short-distance wireless communication method.

The controller 160 may obtain the information about the position of the wireless ultrasound probe 100 by the determined data communication method, and may control the communicator 130 to transmit obtained information about the position of the wireless ultrasound probe 100 to the ultrasound diagnosis apparatus 200. In an embodiment, the controller 160 may update the information about the position of the wireless ultrasound probe 100 that is changed according to a motion of a user using the wireless ultrasound probe 100, and may control the communicator 130 to provide updated information about the position of the wireless ultrasound probe 100 to the ultrasound diagnosis apparatus 200.

The controller 160 may control operation of the wireless power receiver 140 and the battery 150. In an embodiment, the controller 160 checks information about a state of the battery 150 including a remaining amount of the battery 150, a usage time of the battery 150, and a use state of the battery 150, and may transmit an electric signal requesting transmission of wireless power to the ultrasound diagnosis apparatus 200 based on checked information about a state of the battery 150. In an embodiment, the controller 160 may transmit an electric signal requesting the transmission of wireless power to the ultrasound diagnosis apparatus 200 only when the wireless ultrasound probe 100 is not in use.

The controller 160 may be a module including, for example, a central processing unit, a microprocessor, a graphic processing unit, random-access memory (RAM), and read-only memory (ROM). In an embodiment, the controller 160 may be embodied by an application processor (AP). In an embodiment, the controller 160 may be embodied by a hardware element such as an FPGA or ASIC. However, the present disclosure is not limited thereto and the controller 160 may includes constituent elements such as software constituent elements, object-oriented software constituent elements, class constituent elements, and task constituent elements, processes, functions, attributes, procedures, sub-routines, segments of program codes, drivers, firmware, microcodes, circuits, data, databases, data structures, tables, arrays, and variables.

Figure 3:
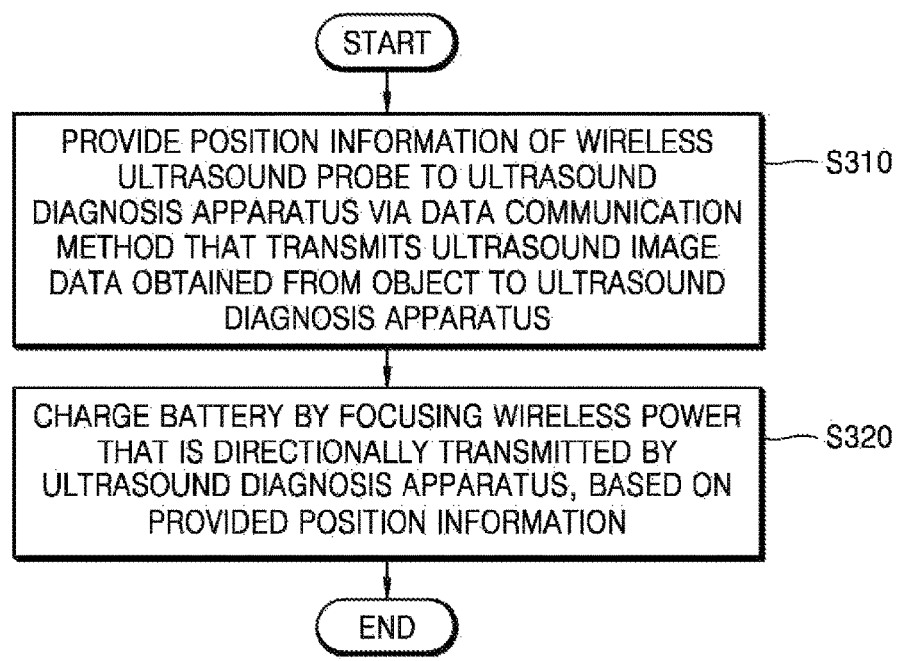
FIG. 3 is a flowchart of a method of charging a wireless ultrasound probe, according to an embodiment.

FIG. 3 is a flowchart of a method of charging the wireless ultrasound probe 100 according to the present embodiment.

In Operation S310, the wireless ultrasound probe 100 provides information about the position of the wireless ultrasound probe 100 to the ultrasound diagnosis apparatus 200 via a data communication method for transmitting ultrasound image data obtained from the object to the ultrasound diagnosis apparatus 200. In an embodiment, the wireless ultrasound probe 100 may determine the type of data configured to be processed by the ultrasound diagnosis apparatus 200, based on the information about the ultrasound diagnosis apparatus 200, and may determine a method of performing data communication with the ultrasound diagnosis apparatus 200. For example, the wireless ultrasound probe 100 may transmit raw data of the object to the ultrasound diagnosis apparatus 200 by a 60 GHz millimeter wave short-distance wireless communication method.

In an embodiment, the wireless ultrasound probe 100 may transmit at least one piece of information about setting of the wireless ultrasound probe 100 including information about identification of the wireless ultrasound probe 100, ultrasound preset setting information, information about a user of the wireless ultrasound probe 100, and information about the object, to the ultrasound diagnosis apparatus 200.

In Operation S320, the wireless ultrasound probe 100 charges the battery 150 by focusing the wireless power that is directionally transmitted by the ultrasound diagnosis apparatus 200, based on the provided position information. In an embodiment, the wireless ultrasound probe 100 may receive wireless power in the form of a magnetic field beam that is directionally transmitted by the ultrasound diagnosis apparatus 200. In an embodiment, the wireless ultrasound probe 100 may charge the battery 150 included in the wireless ultrasound probe 100 by focusing wireless power transmitted by the magnetic resonance method.

Figure 4:
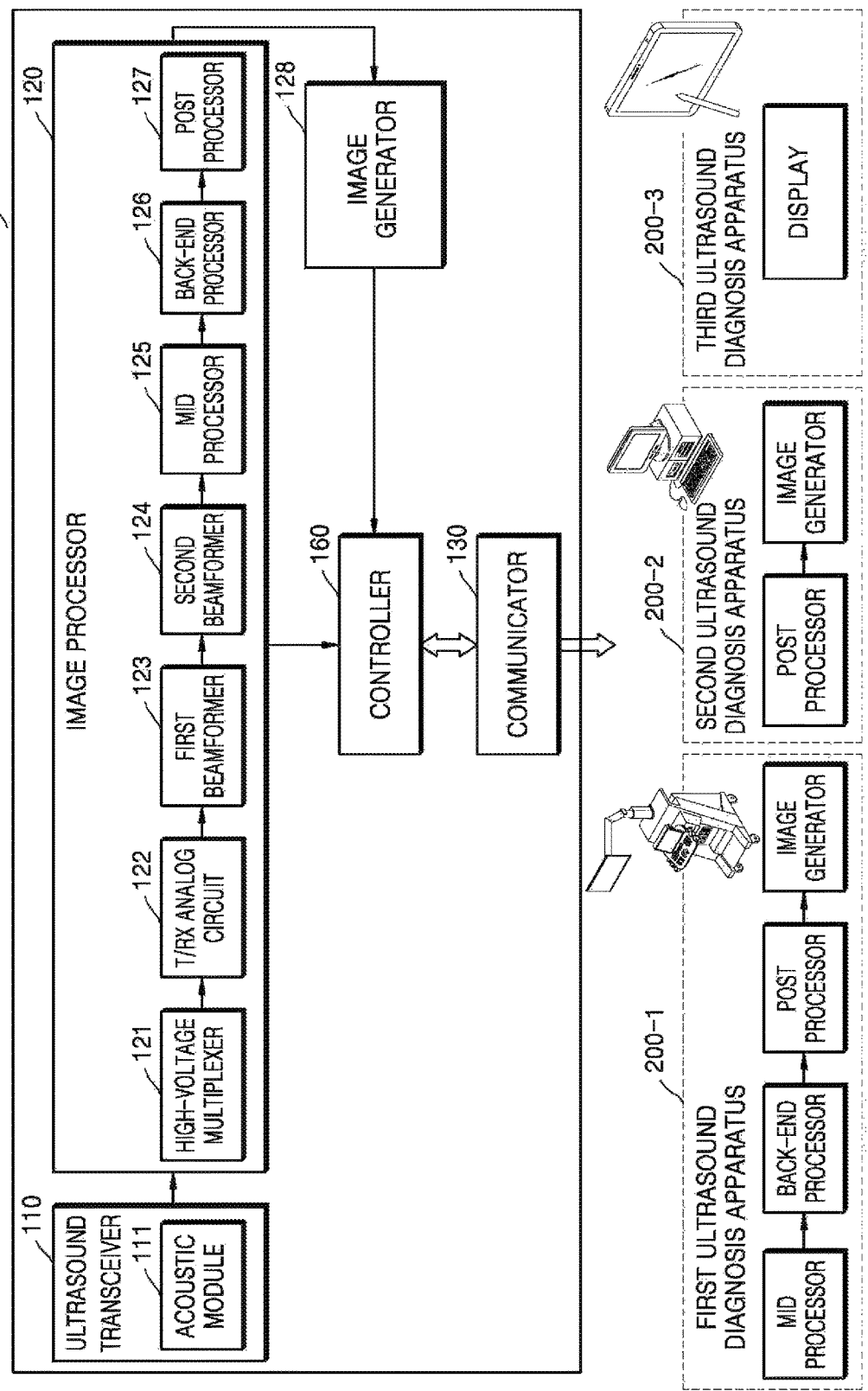
FIG. 4 is a conceptual diagram for explaining a method of communicating between a wireless ultrasound probe and an ultrasound diagnosis apparatus by using a plurality of wireless communication methods, according to an embodiment.

FIG. 4 is a conceptual diagram for explaining a method of communicating between the wireless ultrasound probe 100 according to the present embodiment and the ultrasound diagnosis apparatus 200 by using a plurality of wireless communication methods.

Referring to FIG. 4, the wireless ultrasound probe 100 may include the ultrasound transceiver 110, the image processor 120, an image generator 128, the communicator 130, and the controller 160. However, the structure of the wireless ultrasound probe 100 according to the present embodiment is not limited to the structure of FIG. 4, and the wireless ultrasound probe 100 may include more or less elements than the elements illustrated in FIG. 4. Since the communicator 130 and the controller 160 are the same as the communicator 130 and the controller 160 of FIG. 2, redundant descriptions thereof are omitted.

The ultrasound transceiver 110 may include an acoustic module 111. The acoustic module 111 receives an echo signal reflected from the object. The echo signal reflected from the object may be an ultrasound signal that is an RF signal reflected from the object. The acoustic module 111 may include a plurality of transducers. The transducers may vibrate according to a received electric signal and generate ultrasound waves that are acoustic energy, and may generate an electric signal by processing the acoustic energy reflected from the object.

The image processor 120 may include a high-voltage multiplexer 121, a transceiving (T/RX) analog circuit 122, a first beamformer (BF1) 123, a second beamformer (BF2) 124, a mid processor 125, a back-end processor 126, and a post processor 127.

The high-voltage multiplexer 121 may sequentially select the transducers of the acoustic module 111. The T/RX analog circuit 122 may split a signal to transmit an ultrasound signal to the object and a signal obtained by processing a received echo signal.

The BF1 and BF2 123 and 124 perform a process of focusing the echo signal to check reflection properties of tissues at a desired position of the object from the received echo signal. In an embodiment, the BF1 123 may be an analog beamformer, whereas the BF2 124 may be a digital beamformer.

The mid processor 125 may perform a mid processing operation on a beam formed signal by the BF1 and BF2 123 and 124. For example, the mid processor 125 may control gain with respect to the beamformed signal. The mid processor 125 may perform phase rotation according to dynamic frequency variation on each of a plurality of areas separated based on certain depths, to compensate for frequency variation that is changed according to a depth of the object. Furthermore, the mid processor 125 may perform low-pass filtering.

The back-end processor 126 may detect an envelope with respect to I component data and Q component data output from the mid processor 125.

The post processor 127 may perform digital signal processing (DSP) to generate a Doppler-mode (D-mode) image and a color-mode (C-mode) image.

The image generator 128 may generate an image in the form of being output to the screen from a processed signal.

In an embodiment, the types of data that may be respectively processed in a plurality of ultrasound diagnosis apparatuses 200-1, 200-2, and 200-3 may different from one another. In other words, the ultrasound diagnosis apparatuses 200-1, 200-2, and 200-3 may be generally configured to be capable of generating an ultrasound image from an intermediate signal or image data obtained from any one of the above-described image processing elements 121 to 127. Each of the image processing elements 121 to 127 included in the image processor 120 may be the image processor 120 of the image processor 120 according to the present embodiment. Accordingly, to be used by being connected to the ultrasound diagnosis apparatuses 200-1, 200-2, and 200-3, the wireless ultrasound probe 100 according to the present embodiment may output data suitable for the ultrasound diagnosis apparatuses 200-1, 200-2, and 200-3 according to the types of data that may be respectively processed by the ultrasound diagnosis apparatuses 200-1, 200-2, and 200-3.

The controller 160 may recognize an identifier ID of one of the ultrasound diagnosis apparatuses 200-1, 200-2, and 200-3 that is connected to the wireless ultrasound probe 100. The wireless ultrasound probe 100 may recognize a signal processing operation that may be processed by the ultrasound diagnosis apparatus connected to the wireless ultrasound probe 100, based on the ID of the ultrasound diagnosis apparatus, and the signal processing operation that may be processed by the ultrasound diagnosis apparatus may be processed inside the wireless ultrasound probe 100. Transmission data transmitted by the wireless ultrasound probe 100 to the ultrasound diagnosis apparatus may be image data as a mid processing result or completely processed image data. The ultrasound diagnosis apparatus may perform remaining processing operations that have not been completed with respect to the transmission data, to generate an ultrasound image to be output to the screen or display.

The wireless ultrasound probe 100 may selectively output intermediate data generated in a certain processing operation among a series of processing operations to obtain an ultrasound image with respect to an object from the echo signal received from the object, based on the ID of the ultrasound diagnosis apparatus.

In an embodiment, the first ultrasound diagnosis apparatus 200-1 may perform all signal processing operations, except for the beamforming. Accordingly, when the wireless ultrasound probe 100 is connected to the first ultrasound diagnosis apparatus 200-1, the wireless ultrasound probe 100 may transmit a signal output from the second beamformer 124, as the transmission data, to the first ultrasound diagnosis apparatus 200-1. The wireless ultrasound probe 100 may deactivate the mid processor 125, the back-end processor 126, the post processor 127, and the image generator 128, which perform processing operations after the beamforming.

In an embodiment, when the second ultrasound diagnosis apparatus 200-2 performs processing operations after the back-end processor 126 to display an ultrasound image, the wireless ultrasound probe 100 may generate an output of the back-end processor 126 as the transmission data. In this state, since the wireless ultrasound probe 100 does not need to perform the functions of the post processor 127 and the image generator 128, the post processor 127 and the image generator 128 may be deactivated.

Unlike the first ultrasound diagnosis apparatus 200-1 and the second ultrasound diagnosis apparatus 200-2, the third ultrasound diagnosis apparatus 200-3 is an apparatus that performs only a function of displaying an image without additional image processing function. Accordingly, when the wireless ultrasound probe 100 is connected to the third ultrasound diagnosis apparatus 200-3, the wireless ultrasound probe 100 may transmit a signal output from the image generator 128, as the transmission data, to the third ultrasound diagnosis apparatus 200-3.

In an embodiment, the wireless ultrasound probe 100 may transmit ultrasound image data to the ultrasound diagnosis apparatuses 200-1, 200-2, and 200-3 by a plurality of data communication methods. The wireless ultrasound probe 100 may transmit the transmission data by an appropriate data communication method according to a wireless communication method used by the ultrasound diagnosis apparatuses 200-1, 200-2, and 200-3. In an embodiment, the wireless ultrasound probe 100 may use different data communication methods according to the characteristics of data to be transmitted.

Figure 5:
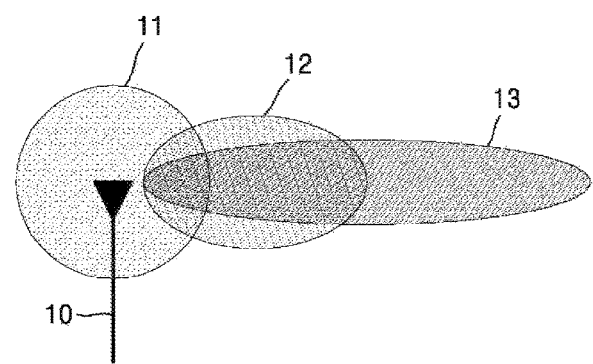
FIG. 5 is a conceptual view for explaining a method of transmitting directional wireless power, according to an embodiment.

FIG. 5 is a conceptual view for explaining a method of transmitting directional wireless power, according to an embodiment.

Referring to FIG. 5, a plurality of beam patterns 11, 12, and 13 are radiated from an antenna 10. The first beam pattern 11 may be an isotropic beam pattern radiated in the form of a sphere radiated in all directions from the antenna 10. The second beam pattern 12 and the third beam pattern 13 may be directional beam patterns having directionality radiated from the antenna 10.

In general, decibel isotropic (dBi) is used as a unit for evaluating gain of the antenna 10. The dBi signifies a ratio between a signal of an antenna having directionality and a signal of an antenna having isotropy. The gain values of the first beam pattern 11, the second beam pattern 12, and the third beam pattern 13 illustrated in FIG. 5 may be the same. In other words, a total amount of energy of a beam pattern isotropically radiated from the antenna 10 (first beam pattern) is the same as a total amount energy of a beam pattern directionally radiated from the antenna 10 (second beam pattern and third beam pattern). Furthermore, for a beam pattern directionally radiated from the antenna 10, the amount of energy of a beam pattern radiated according to a distance.

In beamforming technology according to the present embodiment, the energy of a signal may be intensively converged in one direction by adjusting a radiation pattern of the antenna 10. The beamforming technology purposes efficiently receiving a signal or accurately transmitting a signal in a desired direction. The antenna 10 may have a high gain by forming a beam, compared to an isotropic antenna. In the following description, a method of directionally transmitting wireless power by using the beamforming technology is described with reference to FIGS. 6A to 6C.

Figure 6A:
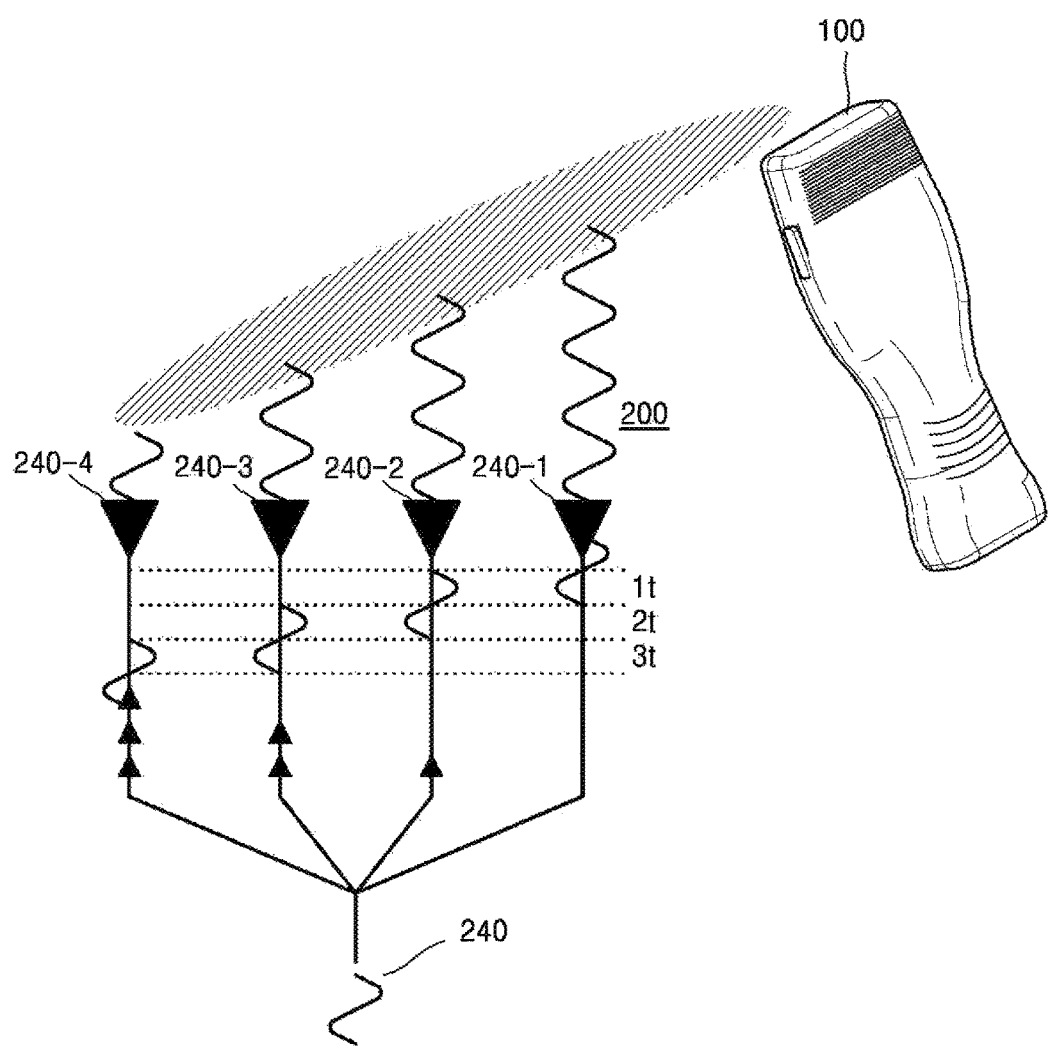

FIG. 6A is a conceptual view for explaining a method of directionally transmitting wireless power to a position of the wireless ultrasound probe 100 by using the beamforming technology, which is performed by the ultrasound diagnosis apparatus 200, according to an embodiment.

Referring to FIG. 6A, the ultrasound diagnosis apparatus 200 may include the wireless power transmitter 240. The wireless power transmitter 240 a first transducer 240-1 to a fourth transducer 240-4. In an embodiment, the first transducer 240-1 to the fourth transducer 240-4 may be phase array transducers for transforming driving signals received from the ultrasound diagnosis apparatus 200 and having different delay times to a wireless power transmission signal. The first transducer 240-1 to the fourth transducer 240-4 are examples presented for convenience of explanation, and the number and shape of the phase array transducers included in the wireless power transmitter 240 are not limited thereto.

The ultrasound diagnosis apparatus 200 may control beam focusing direction and/or angle such that wireless power is focused at a particular position where the wireless ultrasound probe 100 is placed, through timing control of an electric signal applied to each of the first transducer 240-1 to the fourth transducer 240-4. For example, the first transducer 240-1 may receive an input of a driving signal having a delay time of 0, the second transducer 240-2 may receive an input of a driving signal delayed as long as a first delay time 1*t*, the third transducer 240-3 may receive a driving signal delayed as long as a second delay time 2*t*, and the fourth transducer 240-4 may receive a driving signal delayed as long as a third delay time 3*t*, the respective driving signals being received from the ultrasound diagnosis apparatus 200. The ultrasound diagnosis apparatus 200 may sequentially output wireless power by applying a different delay time to each of the first transducer 240-1 to the fourth transducer 240-4, thereby adjusting a focal length of a beam.

The wireless ultrasound probe 100 according to the present embodiment may focus the wireless power directionally transmitted by the ultrasound diagnosis apparatus 200 by the above-described beamforming control method.

FIG. 6B is a block diagram for explaining a method of charging the battery 150 by focusing directional wireless power transmitted by the ultrasound diagnosis apparatus 200, which is performed by the wireless ultrasound probe 100, according to an embodiment.

Referring to FIG. 6B, the wireless ultrasound probe 100 may include the communicator 130, the wireless power receiver 140, the battery 150, and the controller 160, whereas the ultrasound diagnosis apparatus 200 may include a communicator 230, the wireless power transmitter 240, and a controller 250. However, this is merely for convenience of explanation, and the wireless ultrasound probe 100 and the ultrasound diagnosis apparatus 200 may include more or less constituent elements than those illustrated in FIG. 6B. Since the communicator 130, the wireless power receiver 140, the battery 150, and the controller 160 are respectively the same as the communicator 130, the wireless power receiver 140, the battery 150, and the controller 160 illustrated in FIG. 2, redundant descriptions thereof are omitted.

The ultrasound diagnosis apparatus 200 may be wirelessly connected to the wireless ultrasound probe 100 via the communicator 230. The communicator 230 may perform data communication with the communicator 130 of the wireless ultrasound probe 100 by at least one of short-distance communication methods, for example, LAN, Wi-Fi, Bluetooth, Zigbee, WFD, UWB, IrDA, BLE, NFC, Wibro, WiMAX, SWAP, WiGig, and RF communications.

In an embodiment, the communicator 230 may perform wireless data communication with the wireless ultrasound probe 100 by the 60 GHz millimeter wave short-distance wireless communication method. In an embodiment, the communicator 230 may obtain the information about the position of the wireless ultrasound probe 100 from the communicator 130 of the wireless ultrasound probe 100, based on the control of the controller 250.

The ultrasound diagnosis apparatus 200 may directionally transmit wireless power to the wireless ultrasound probe 100 via the wireless power transmitter 240. In an embodiment, the wireless power transmitter 240 may transmit wireless power by the magnetic resonance method. In an embodiment, the wireless power transmitter 240 may include the transducers 240-1 to 240-*n*. In an embodiment, the transducers 240-1 to 240-*n* may be phase array transducers for transforming driving signals having different delay times to a wireless power transmission signal. The transducers 240-1 to 240-*n* may be arranged in a two-dimensional matrix form as illustrated in FIG. 6B. However, the arrangement of the transducers 240-1 to 240-*n* is not limited to the illustration of FIG. 6B. The transducers 240-1 to 240-*n* may be arranged in a circular, rectangular, or diamond shape.

The controller 250 may adjust an order of driving signals by applying a calculated delay time to each of the transducers 240-1 to 240-*n*, such that the transducers 240-1 to 240-*n* may output wireless power in a particular order. The controller 250 may control a focusing direction and/or angle of wireless power by differently applying the order of driving signals to each of the transducers 240-1 to 240-*n*. In other words, the controller 250 may control a delay time of a driving signal by using a beamsteering technology and may set a focal position where beams including wireless power are focused overlapping one another. In an embodiment, the controller 250 may set a focal position where wireless power is focused at a position corresponding to the information about the position of the wireless ultrasound probe 100 received from the communicator 230 and may control the wireless power transmitter 240 to transmit wireless power to the set focal position.

Figure 6C:
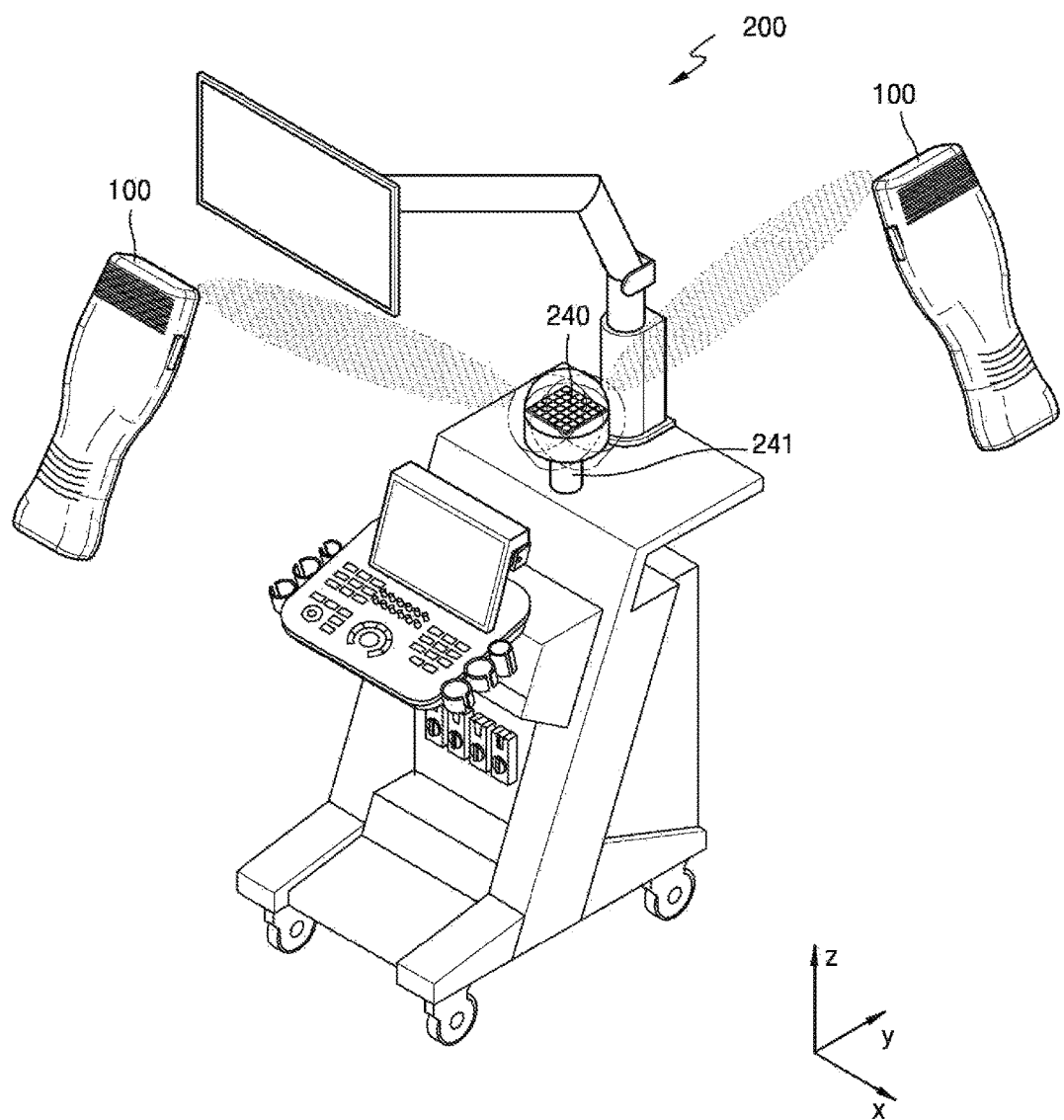

FIG. 6C is a conceptual view illustrating a method of receiving directional wireless power from the ultrasound diagnosis apparatus 200, which is performed by the wireless ultrasound probe 100, according to an embodiment.

Referring to FIG. 6C, the ultrasound diagnosis apparatus 200 may include the wireless power transmitter 240 and the direction controller 241. Since the ultrasound diagnosis apparatus 200 of FIG. 6C is the same as the ultrasound diagnosis apparatus 200 of FIG. 6B, except for further including the direction controller 241, a redundant description thereof is omitted.

The direction controller 241 may be physically connected to the wireless power transmitter 240 and may change a wireless power transmission direction of the wireless power transmitter 240. In an embodiment, the direction controller 241 may include a motor capable of changing the direction of the wireless power transmitter 240 by 360°. The direction controller 241 may move the wireless power transmitter 240 in at least one direction among a first direction (X direction), a second direction (Y direction) that is perpendicular to the first direction, and a third direction (Z direction) that is perpendicular to each of the first direction (X direction) and the second direction (Y direction). Furthermore, the direction controller 241 may rotate the wireless power transmitter 240 around at least one direction of the first direction (X direction), the second direction (Y direction), and the third direction (Z direction).

The controller 250 may control the direction controller 241, based on the information about the position of the wireless ultrasound probe 100 obtained from the communicator 130 of the wireless ultrasound probe 100, so that the wireless power transmitted by the wireless power transmitter 240 may be directionally transmitted toward the position of the wireless ultrasound probe 100. For example, when the wireless ultrasound probe 100 is located at the right side of the ultrasound diagnosis apparatus 200, the controller 250 may control the direction controller 241 so that the wireless power transmitter 240 faces the wireless ultrasound probe 100 located at the right side. Likewise, when the wireless ultrasound probe 100 is located at the left side of the ultrasound diagnosis apparatus 200, the controller 250 may control the direction controller 241 so that the wireless power transmitter 240 faces the wireless ultrasound probe 100 located at the left side. The controller 250 is not limited to the above-described left and right sides. Accordingly, the controller 250 may control the direction controller 241 so that the wireless power transmitter 240 is rotated in any direction and/or by any angle around 360° with respect to a direction corresponding to the position of the wireless ultrasound probe 100.

In the present embodiment, the ultrasound diagnosis apparatus 200 not only uses a beamsteering method by which different driving signals are generated by calculating a delay time of the wireless power transmitter 240, but also includes the direction controller 241 that may change the direction of the wireless power transmitter 240, thereby directionally transmitting wireless power toward the position of the wireless ultrasound probe 100. Accordingly, efficiency in the transmission of wireless power to the wireless ultrasound probe 100 may be improved.

FIG. 7 is a flowchart of a method of charging the battery 150 by receiving directional wireless power from the ultrasound diagnosis apparatus 200, which is performed by the wireless ultrasound probe 100, according to an embodiment.

In Operation S710, the wireless ultrasound probe 100 transmit a session forming request signal to the ultrasound diagnosis apparatus 200 to form a session with the ultrasound diagnosis apparatus 200. The ultrasound diagnosis apparatus 200 receiving the session forming request signal may respond to the wireless ultrasound probe 100 confirming that the session forming request signal is received. In Operation S712, the wireless ultrasound probe 100 may receive a session forming confirmation signal from the ultrasound diagnosis apparatus 200.

In an embodiment, the wireless ultrasound probe 100 may transceive data by being wirelessly connected to the ultrasound diagnosis apparatus 200. The wireless connection between the wireless ultrasound probe 100 and the ultrasound diagnosis apparatus 200 may signify a session is formed as the wireless ultrasound probe 100 and the ultrasound diagnosis apparatus 200 are paired with each other. The "session" signifies a logical connection for communication between the ultrasound diagnosis apparatus 200 and the wireless ultrasound probe 100. To form a session, a process of recognizing each other by exchanging messages between the ultrasound diagnosis apparatus 200 and the wireless ultrasound probe 100 may be necessary. Accordingly, in order to form a session between the wireless ultrasound probe 100 and the ultrasound diagnosis apparatus 200, the wireless ultrasound probe 100 may transmit a session forming request signal to the ultrasound diagnosis apparatus 200 and may receive a session forming confirmation signal from the ultrasound diagnosis apparatus 200.

In Operation S720, the wireless ultrasound probe 100 determines a data communication method by which the wireless ultrasound probe 100 is wirelessly connected to the ultrasound diagnosis apparatus 200. In Operations S710 and S712, the wireless ultrasound probe 100 may obtain information about a bandwidth of a communication channel through the session formed between the ultrasound diagnosis apparatus 200 and the wireless ultrasound probe 100. For example, the wireless ultrasound probe 100 may extract the information about a bandwidth of a communication channel from the session forming confirmation signal received from the ultrasound diagnosis apparatus 200. After forming a session with the ultrasound diagnosis apparatus 200, the wireless ultrasound probe 100 may obtain the information about a bandwidth of a communication channel after a certain period of time or at certain time period.

The information about a bandwidth of a communication channel may be, for example, a bandwidth value of a communication channel, or may include information about an operation state of the wireless ultrasound probe 100, information about an operation state of the ultrasound diagnosis apparatus 200, and a test packet for measuring a bandwidth. The wireless ultrasound probe 100 may obtain the information about a bandwidth of a communication channel by receiving a test packet from the ultrasound diagnosis apparatus 200 and analyzing the test packet. The information about a bandwidth of a communication channel may include at least one parameter value related to the quality of an ultrasound image determined by the ultrasound diagnosis apparatus 200 based on the bandwidth of a communication channel, and a transmission speed of a frame forming the ultrasound image.

In an embodiment, the wireless ultrasound probe 100 may determine the type of data to be processed by the ultrasound diagnosis apparatus 200 based on the information about the bandwidth of a communication channel with the ultrasound diagnosis apparatus 200, and may determine a method of performing data communication with the ultrasound diagnosis apparatus 200. For example, the wireless ultrasound probe 100 may transmit raw data of an object to the ultrasound diagnosis apparatus 200 by the 60 GHz millimeter wave short-distance wireless communication method.

In Operation S730, the wireless ultrasound probe 100 provides the information about the position of the wireless ultrasound probe 100 to the ultrasound diagnosis apparatus 200. In an embodiment, the wireless ultrasound probe 100 may provide the information about the position of the wireless ultrasound probe 100 to the ultrasound diagnosis apparatus 200 by the data communication method determined in the operation S720. In an embodiment, the wireless ultrasound probe 100 may transmit the information about the position of the wireless ultrasound probe 100 to the ultrasound diagnosis apparatus 200 by the 60 GHz millimeter wave short-distance wireless communication method.

In Operation S740, the ultrasound diagnosis apparatus 200 recognizes the position of the wireless ultrasound probe 100.

In Operation S750, the ultrasound diagnosis apparatus 200 transmits directional wireless power to the wireless ultrasound probe 100. The ultrasound diagnosis apparatus 200 may directionally transmit wireless power to the position of the wireless ultrasound probe 100, based on the information about the position of the wireless ultrasound probe 100 recognized in the operation S740. In an embodiment, the ultrasound diagnosis apparatus 200 may directionally transmit wireless power in the form of a magnetic field beam to the wireless ultrasound probe 100. In an embodiment, the ultrasound diagnosis apparatus 200 may directionally transmit wireless power to the wireless ultrasound probe 100 by the beamsteering method. In an embodiment, the ultrasound diagnosis apparatus 200 may transmit wireless power to the wireless ultrasound probe 100 by the magnetic resonance method.

In Operation S760, the wireless ultrasound probe 100 focuses wireless power transmitted by the ultrasound diagnosis apparatus 200. In an embodiment, the wireless ultrasound probe 100 may focus magnetic resonance wireless power that is received from the ultrasound diagnosis apparatus 200.

In Operation S770, the wireless ultrasound probe 100 charges the battery 150 included in the wireless ultrasound probe 100.

FIG. 8 is a flowchart of a method of providing position information to the ultrasound diagnosis apparatus 200, which is performed by the wireless ultrasound probe 100, according to an embodiment.

In Operation S810, the wireless ultrasound probe 100 recognizes a movement of the wireless ultrasound probe 100. In an embodiment, while the object is checked by transmitting an ultrasound wave is transmitted to the object and receiving the echo signal reflected from the object, the wireless ultrasound probe 100 may be moved by the manipulation of a user. The wireless ultrasound probe 100 may recognized the movement of the wireless ultrasound probe 100 according to the manipulation of a user.

In Operation S820, the wireless ultrasound probe 100 updates position information by tracking the position of the wireless ultrasound probe 100. In an embodiment, the wireless ultrasound probe 100 may track in real time the position of the wireless ultrasound probe 100 according to the manipulation of a user. The wireless ultrasound probe 100 may update position information previously stored in the wireless ultrasound probe 100 by using the position information that is tracked in real time.

In Operation S830, the wireless ultrasound probe 100 provides updated position information to the ultrasound diagnosis apparatus 200. In an embodiment, the wireless ultrasound probe 100 may transmit the updated information about the position of the wireless ultrasound probe 100 to the ultrasound diagnosis apparatus 200, by the data communication method used when the wireless ultrasound probe 100 is wirelessly connected to the ultrasound diagnosis apparatus 200. In an embodiment, the wireless ultrasound probe 100 may transmit the updated position information to the ultrasound diagnosis apparatus 200 by the 60 GHz millimeter wave short-distance wireless communication method.

In Operation S840, the ultrasound diagnosis apparatus 200 updates the information about the position of the wireless ultrasound probe 100.

As the wireless ultrasound probe 100 according to the present embodiment provides updated position information to the ultrasound diagnosis apparatus 200 through data communication even when the wireless ultrasound probe 100 is moved according to the manipulation of a user, the ultrasound diagnosis apparatus 200 may transmit directional wireless power based on the updated position information.

FIG. 9 is a flowchart of a method of charging the battery 150 of the wireless ultrasound probe 100 by receiving directional wireless power from the ultrasound diagnosis apparatus 200 based on information about a state of the battery 150, according to an embodiment.

In Operation S910, the ultrasound diagnosis apparatus 200 requests conformation of the information about a state of the battery 150 of the wireless ultrasound probe 100. In an embodiment, the ultrasound diagnosis apparatus 200 may transmit an electric signal requesting confirmation of the information about a state of the battery 150 to the wireless ultrasound probe 100 by the data communication method used for wirelessly connecting the ultrasound diagnosis apparatus 200 to the wireless ultrasound probe 100. In an embodiment, the ultrasound diagnosis apparatus 200 may transmit an electric signal requesting confirmation of the information about a state of the battery 150 to the wireless ultrasound probe 100 by the 60 GHz millimeter wave short-distance wireless communication method.

In Operation S920, the wireless ultrasound probe 100 checks the information about a state of the battery 150. The information about a state of the battery 150 may include the remaining amount of the battery 150, the usage time of the battery 150, and the use state of the battery 150 included in the wireless ultrasound probe 100.

In Operation S930, the wireless ultrasound probe 100 transmits the information about a state of the battery 150 to the ultrasound diagnosis apparatus 200. In an embodiment, the wireless ultrasound probe 100 may transmit the information about a state of the battery 150 to the ultrasound diagnosis apparatus 200 by the data communication method used for connecting the wireless ultrasound probe 100 to the ultrasound diagnosis apparatus 200.

In Operation S940, the wireless ultrasound probe 100 requests battery charge from the ultrasound diagnosis apparatus 200, based on the information about a state of the battery 150. In an embodiment, the wireless ultrasound probe 100 may transmit an electric signal requesting battery charge to the ultrasound diagnosis apparatus 200 by the data communication method used for connecting the wireless ultrasound probe 100 to the ultrasound diagnosis apparatus 200. The wireless ultrasound probe 100 may request transmission of wireless power from the ultrasound diagnosis apparatus 200 based on at least one piece of information of the remaining amount of the battery 150, the usage time of the battery 150, and the use state of the battery 150.

In Operation S940, the wireless ultrasound probe 100 may provide an alarm signal to a user when the remaining amount of the battery 150 is less than a predetermined value. In an embodiment, the wireless ultrasound probe 100 may compare the remaining amount of the battery 150 with the predetermined value, based on the information about a state of the battery 150 checked in the operation S920. The wireless ultrasound probe 100 may include an alarm display portion for providing an alarm signal to a user using an acoustic signal such as alarm sound or a visual signal such as text when the remaining amount of the battery 150 is less than the predetermined value.

In Operation S950, the ultrasound diagnosis apparatus 200 analyzes the information about a state of the battery 150 of the wireless ultrasound probe 100. In an embodiment, the ultrasound diagnosis apparatus 200 may analyze at least one of the remaining amount of the battery 150, the usage time of the battery 150, and the use state of the battery 150 of the wireless ultrasound probe 100.

In Operation S960, the ultrasound diagnosis apparatus 200 transmits directional wireless power to the wireless ultrasound probe 100. In Operation S970, the wireless ultrasound probe 100 focuses the wireless power transmitted by the ultrasound diagnosis apparatus 200. In Operation S980, the wireless ultrasound probe 100 charges the battery 150 included in the wireless ultrasound probe 100.

Since the operations S960 to S980 are respectively the same as the operations S750 to S770 described above with reference to FIG. 7, redundant descriptions thereof are omitted.

Figure 10:
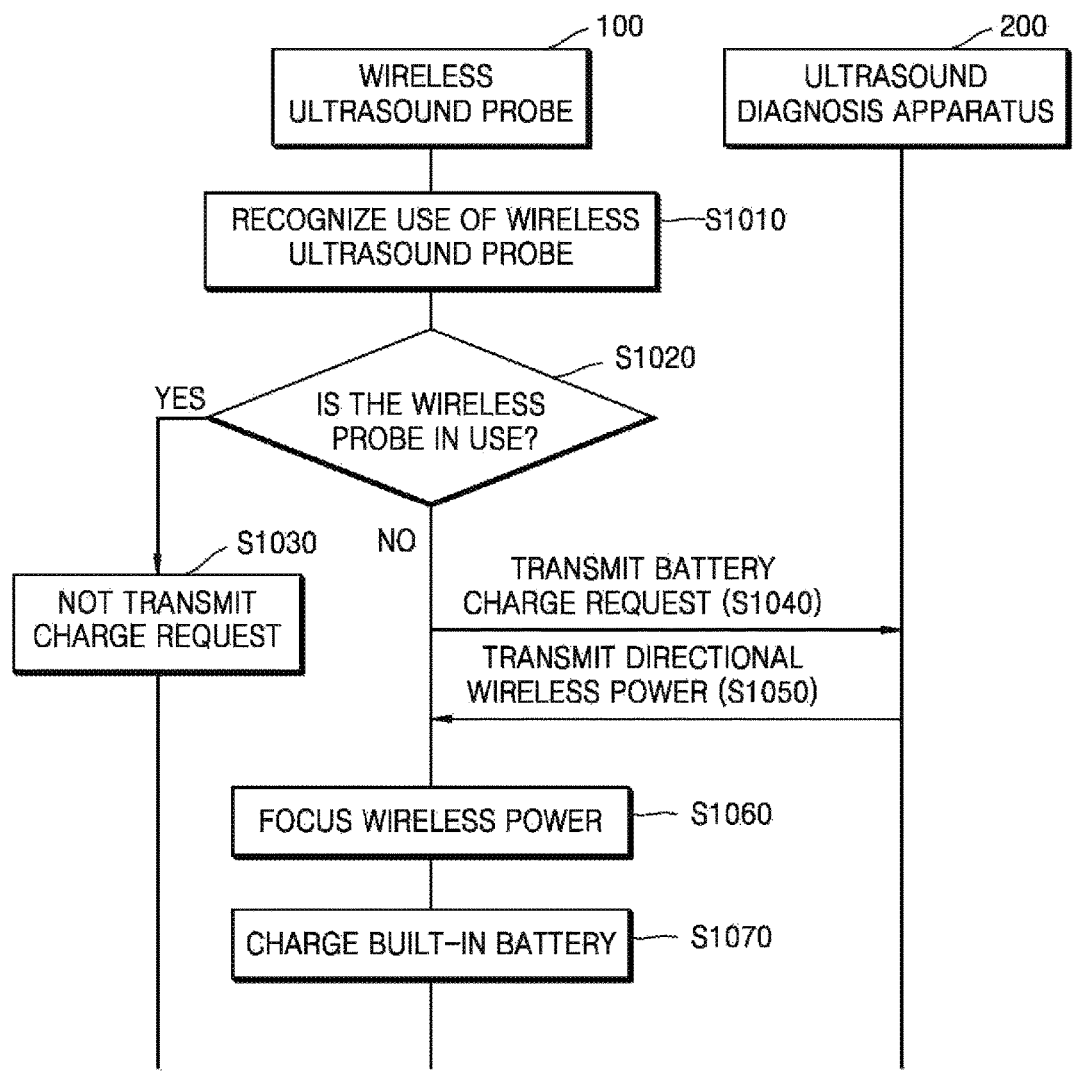
FIG. 10 is a flowchart of a method of charging a battery of a wireless ultrasound probe by receiving directional wireless power from an ultrasound diagnosis apparatus based on a use of the wireless ultrasound probe, according to an embodiment.

FIG. 10 is a flowchart of a method of charging the battery 150 of the wireless ultrasound probe 100 by receiving directional wireless power from the ultrasound diagnosis apparatus 200 based on a use of the wireless ultrasound probe 100, according to an embodiment.

In Operation S1010, the wireless ultrasound probe 100 recognizes a use of the wireless ultrasound probe 100. In an embodiment, the wireless ultrasound probe 100 may recognize a movement of the wireless ultrasound probe 100 according to the manipulation of a user while checking the object.

In Operation S1020, the wireless ultrasound probe 100 determines whether the wireless ultrasound probe 100 is in use. If the wireless ultrasound probe 100 recognizes that the wireless ultrasound probe 100 is in use, the wireless ultrasound probe 100 does not transmit a request to charge the battery 150 to the ultrasound diagnosis apparatus 200 (S1030). In an embodiment, when recognizing that the wireless ultrasound probe 100 is in use, the wireless ultrasound probe 100 may not transmit an electric signal including a request to transmit wireless power from the ultrasound diagnosis apparatus 200.

In Operation S1020, when the wireless ultrasound probe 100 recognizes that the wireless ultrasound probe 100 is not in use (unused), the wireless ultrasound probe 100 requests battery charge from the ultrasound diagnosis apparatus 200 (S1040). In an embodiment, the wireless ultrasound probe 100 may transmit an electric signal requesting battery charge by the data communication method used for connecting the wireless ultrasound probe 100 to the ultrasound diagnosis apparatus 200.

In Operation S1050, the ultrasound diagnosis apparatus 200 transmit directional wireless power to the wireless ultrasound probe 100. In Operation S1060, the wireless ultrasound probe 100 focuses wireless power. In Operation S1070, the wireless ultrasound probe 100 charges the battery 150.

Since the operations S1050 to S1070 are respectively the same as the operations S750 to S770 described above with reference to FIG. 7, redundant descriptions thereof are omitted.

Accordingly, in the method of charging the wireless ultrasound probe 100 according to the present embodiment, since wireless power is received from the ultrasound diagnosis apparatus 200 only when the wireless ultrasound probe 100 is not in use, an influence on a user using the wireless ultrasound probe 100 and/or a patient may be reduced.

Figure 11A:
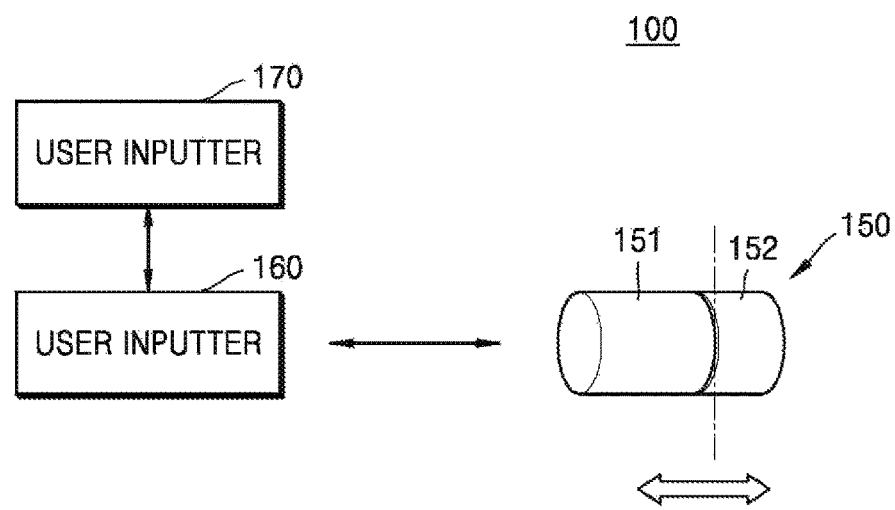
FIGS. 11A and 11B are conceptual views for explaining a method of dividing capacity of a battery of a wireless ultrasound probe and setting an order of discharge of the battery, according to an embodiment.
Figure 11B:
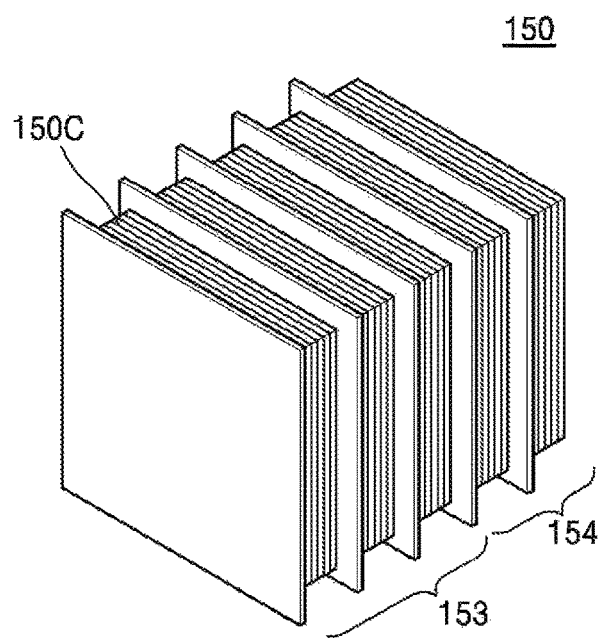

FIGS. 11A and 11B are conceptual views for explaining a method of dividing capacity of the battery 150 of the wireless ultrasound probe 100 and setting an order of discharge of the battery 150, according to an embodiment.

Referring to FIG. 11A, the controller 160 of the wireless ultrasound probe 100 may divide the capacity of the battery 150 and may set an order of discharge. The controller 160 may divide the capacity of the battery 150 into the capacity of a first battery 151 and the capacity of a second battery 152. In an embodiment, the capacity of the first battery 151 may be greater than the capacity of the second battery 152. However, the present disclosure is not limited thereto, and the capacity of the first battery 151 may be less than the second battery 152 or the capacity of the first battery 151 and the capacity of the second battery 152 may be the same.

The controller 160 may set an order of discharge between the first battery 151 and the second battery 152 during a use of the wireless ultrasound probe 100. For example, while a user uses the wireless ultrasound probe 100 to check the object, the first battery 151 is first discharged and the second battery 152 may not be discharged. In this case, the first battery 151 may operate as a battery for use only, whereas the second battery 152 may operate as a battery for discharge only. In an embodiment, when the first battery 151 is completely discharged, the controller 160 may set an order of discharge so that the second battery 152 is discharged. In an embodiment, when the wireless ultrasound probe 100 focuses wireless power received from the ultrasound diagnosis apparatus 200, the controller 160 may set an order of discharge so that the second battery 152 is primarily charged.

In the embodiment illustrated in FIG. 11A, the wireless ultrasound probe 100 may further include a user input portion 170. The user input portion 170 may receive a user input to divide the capacity of the battery 150 and set an order of discharge. For example, the user input portion 170 may receive a user input for setting the capacity of the first battery 151 to about 60% of a total capacity of the battery 150, and the capacity of the second battery 152 to about 40% of the total capacity of the battery 150. Furthermore, the user input portion 170 may receive a user input to set an order of discharge of the battery 150 such that the first battery 151 is primarily discharged compared to the second battery 152 while the wireless ultrasound probe 100 is used to check the object.

The controller 160 may divide the capacity and set the order of discharge of the battery 150, based on the dividing of capacity and the setting of an order of discharge of the battery 150 received from the user input portion 170.

In the checking of the object using the wireless ultrasound probe 100, an amount of power used for transmitting an ultrasound wave to the object and receiving an echo signal reflected from the object is relatively greater than an amount of power used for transmitting ultrasound image data to the ultrasound diagnosis apparatus 200. In an embodiment, as the capacity of the battery 150 of the wireless ultrasound probe 100 is divided and an order of discharge is set with respect to the divided capacity of the battery 150, a minimum amount of power to be used for transmitting ultrasound image data between the wireless ultrasound probe 100 and the ultrasound diagnosis apparatus 200 may be secured.

Referring to FIG. 11B, the battery 150 of the wireless ultrasound probe 100 may include a plurality of battery cells 150C. The controller 160 may set one part of the battery cells 150C to a first battery cell 153 and the other part of the battery cells 150C to a second battery cell 154. In an embodiment, the number of the battery cells 150C included in the first battery cell 153 may be greater than the number of the battery cells 150C included in the second battery cell 154. However, the number of the battery cells 150C included in the first battery cell 153 or the second battery cell 154 is not limited to the above-described example.

The controller 160 may set an order of discharge of the battery cells 150C while the object is checked by using the wireless ultrasound probe 100. For example, the first battery cell 153 may be set to operate as a battery cell for use only, whereas the second battery cell 154 may be set to operate as a battery cell for charge only. In an embodiment, when the first battery cell 153 is completely discharged, the controller 160 may set an order of discharge so that the second battery cell 154 is discharged.

Figure 12:
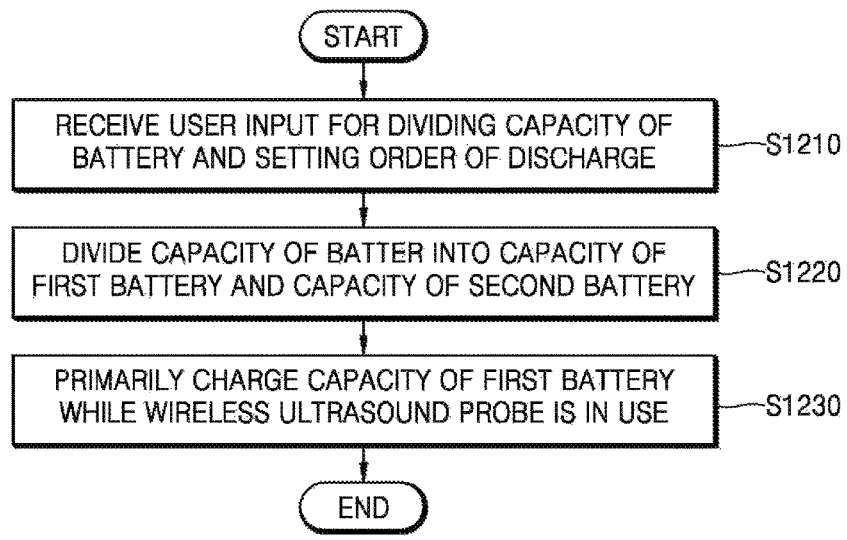
FIG. 12 is a flowchart of a method of dividing capacity of a battery of a wireless ultrasound probe and setting an order of discharge, according to an embodiment.

FIG. 12 is a flowchart of a method of dividing capacity of the battery 150 of the wireless ultrasound probe 100 and setting an order of discharge, according to an embodiment.

In Operation S1210, the wireless ultrasound probe 100 receives a user input to divide the capacity of the battery 150 and set an order of discharge of the battery 150. In an embodiment, the wireless ultrasound probe 100 may include a user input portion for receiving the user input to divide the capacity of the battery 150 and set an order of discharge of the battery 150.

In Operation S1220, the wireless ultrasound probe 100 divides the capacity of the battery 150 into the capacity of a first battery and the capacity of a second batter based on a user input. For example, the wireless ultrasound probe 100 may set the capacities of the first and second batteries based on a user input to set about 60% of a total capacity of the battery 150 to the capacity of the first battery and about 40% of the total capacity of the battery 150 to the capacity of the second battery.

In Operation S1230, the wireless ultrasound probe 100 primarily discharges the capacity of the first battery while the wireless ultrasound probe 100 is in use. In an embodiment, the wireless ultrasound probe 100 may set the capacity of the first battery to be primarily discharged based on the user input while the object is checked by using the wireless ultrasound probe 100. In an embodiment, the wireless ultrasound probe 100 may be set the second battery to be primarily charged when wireless power is transmitted by the ultrasound diagnosis apparatus 200.

Figure 13:
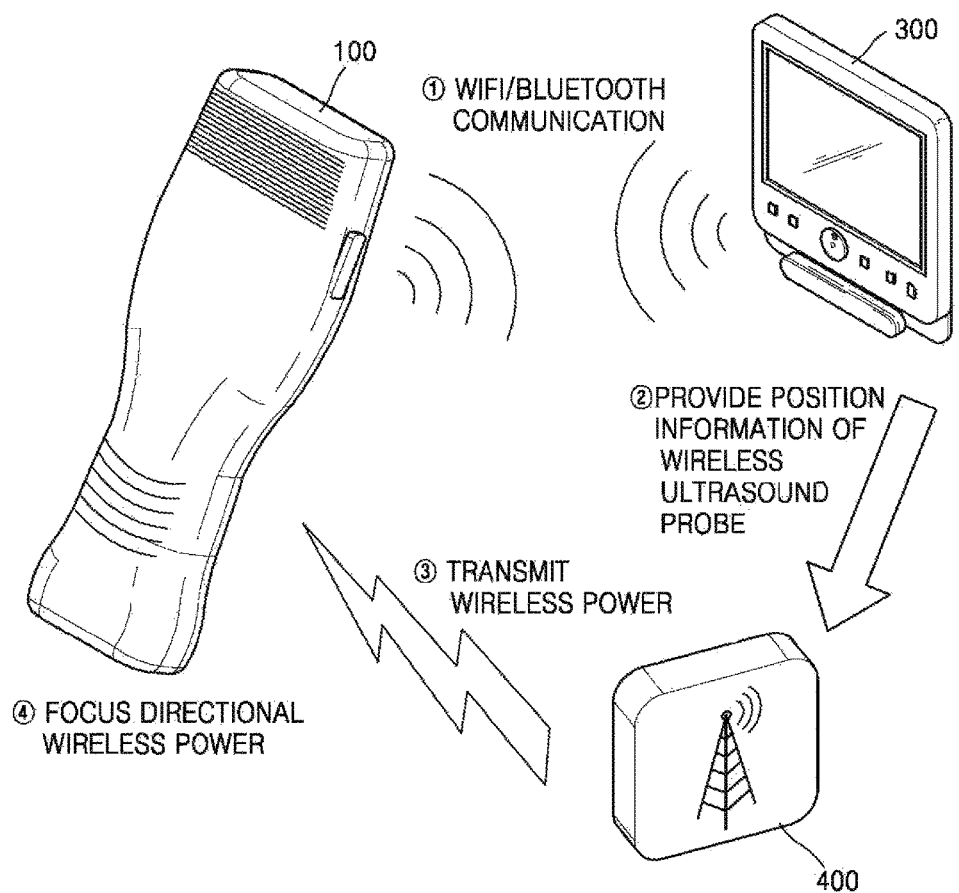
FIG. 13 is a conceptual view for explaining a method of charging a wireless ultrasound probe, according to an embodiment.

FIG. 13 is a conceptual view for explaining a method of charging the wireless ultrasound probe 100, according to an embodiment.

Referring to FIG. 13, the wireless ultrasound probe 100 may be wirelessly connected to an ultrasound image display apparatus 300 via Wi-Fi or Bluetooth and may receive wireless power from a directional wireless power unit 400. Since the wireless ultrasound probe 100 is the same as the wireless ultrasound probe 100 described above with reference to FIGS. 1 and 2, a redundant description thereof is omitted.

The ultrasound image display apparatus 300 is an apparatus for receiving and displaying an ultrasound image generated from the wireless ultrasound probe 100. In an embodiment, the ultrasound image display apparatus 300 may be an apparatus for embodying only an image display function without a separate image processing function. In other words, the ultrasound image display apparatus 300 may be an apparatus that receives an image from the wireless ultrasound probe 100 and displays a received image on the screen without additional processing. The ultrasound image display apparatus 300 may include, for example, the PACS viewer, the HCU, the smart phone, laptop computer, the PDA, or the tablet PC, but not limited thereto.

The wireless ultrasound probe 100 may perform data communication with the ultrasound image display apparatus 300 by at least one of short-distance communication methods, for example, LAN, Wi-Fi, Bluetooth, Zigbee, WFD, UWB, IrDA, BLE, NFC, Wibro, WiMAX, SWAP, WiGig, and RF communications. In an embodiment, the wireless ultrasound probe 100 may perform wireless data communication with the ultrasound image display apparatus 300 by an 802.11n (802.11Ac) standard Wi-Fi communication method capable of directional communication.

When the wireless ultrasound probe 100 is wirelessly connected to the ultrasound image display apparatus 300, the wireless ultrasound probe 100 may generate a final ultrasound image by image-processing an echo signal obtained from the object. Referring to FIG. 4 altogether, in the wireless ultrasound probe 100, the ultrasound transceiver 110 may transmit an ultrasound wave to the object and receive the echo signal reflected from the object, the image processor 120 forms ultrasound image data by image processing the echo signal, and the image generator 128 may generate an ultrasound image. In this case, all image processing elements included in the image processor 120, that is, the high-voltage multiplexer 121, the T/RX analog circuit 122, the first beamformer 123, the second beamformer 124, the mid processor 125, the back-end processor 126, and the post processor 127 (see FIG. 4) may be activated.

In an embodiment, the wireless ultrasound probe 100 may transmit an ultrasound image to the ultrasound image display apparatus 300 by the 802.11n (802.11Ac) standard WIFI communication method capable of directional communication. However, the present disclosure is not limited thereto, and the wireless ultrasound probe 100 may transmit an ultrasound image to the ultrasound image display apparatus 300 by the short-distance communication method including Bluetooth.

The wireless ultrasound probe 100 may provide the information about the position of the wireless ultrasound probe 100 to the ultrasound image display apparatus 300. In an embodiment, the wireless ultrasound probe 100 may transmit the information about the position of the wireless ultrasound probe 100 to the ultrasound image display apparatus 300 by the short-distance communication method for wirelessly connecting the wireless ultrasound probe 100 to the ultrasound image display apparatus 300.

The ultrasound image display apparatus 300 may provide the information about the position of the wireless ultrasound probe 100 to the directional wireless power unit 400. In an embodiment, the ultrasound image display apparatus 300 may transmit the information about the position of the wireless ultrasound probe 100 to the directional wireless power unit 400 by at least one of short-distance communication methods, for example, LAN, Wi-Fi, Bluetooth, Zigbee, WFD, UWB, IrDA, BLE, NFC, Wibro, WiMAX, SWAP, WiGig, and RF communications.

In an embodiment, the ultrasound image display apparatus 300 and the directional wireless power unit 400 may be integrally formed.

The directional wireless power unit 400 transmits wireless power to the wireless ultrasound probe 100. In an embodiment, the directional wireless power unit 400 may directionally transmit wireless power toward the position of the wireless ultrasound probe 100, based on the information about the position of the wireless ultrasound probe 100 obtained from the ultrasound image display apparatus 300. In an embodiment, the directional wireless power unit 400 may transmit wireless power to the wireless ultrasound probe 100 by a directional beamfocusing method using the wireless power transmission module including a retrodirective beamforming antenna. In an embodiment, the directional wireless power unit 400 may transmit wireless power to the wireless ultrasound probe 100 by the magnetic resonance method.

The wireless ultrasound probe 100 may charge the battery 150 included in the wireless ultrasound probe 100 by focusing the wireless power that is directionally transmitted. In an embodiment, the wireless ultrasound probe 100 may charge the battery 150 of the wireless ultrasound probe 100 by focusing a directional magnetic field.

The wireless ultrasound probe 100 according to the present embodiment, unlike the embodiment illustrated in FIG. 1, may receive wireless power from the directional wireless power unit 400 that is provided separately, even when the wireless ultrasound probe 100 is wirelessly connected to the ultrasound image display apparatus 300 that simply displays an image without generating an ultrasound image. Accordingly, according to the present embodiment, when the wireless ultrasound probe 100 is wirelessly connected to a portable or compact ultrasound image display apparatus, an efficiency of charging the wireless ultrasound probe 100 may be improved.

Figure 14:
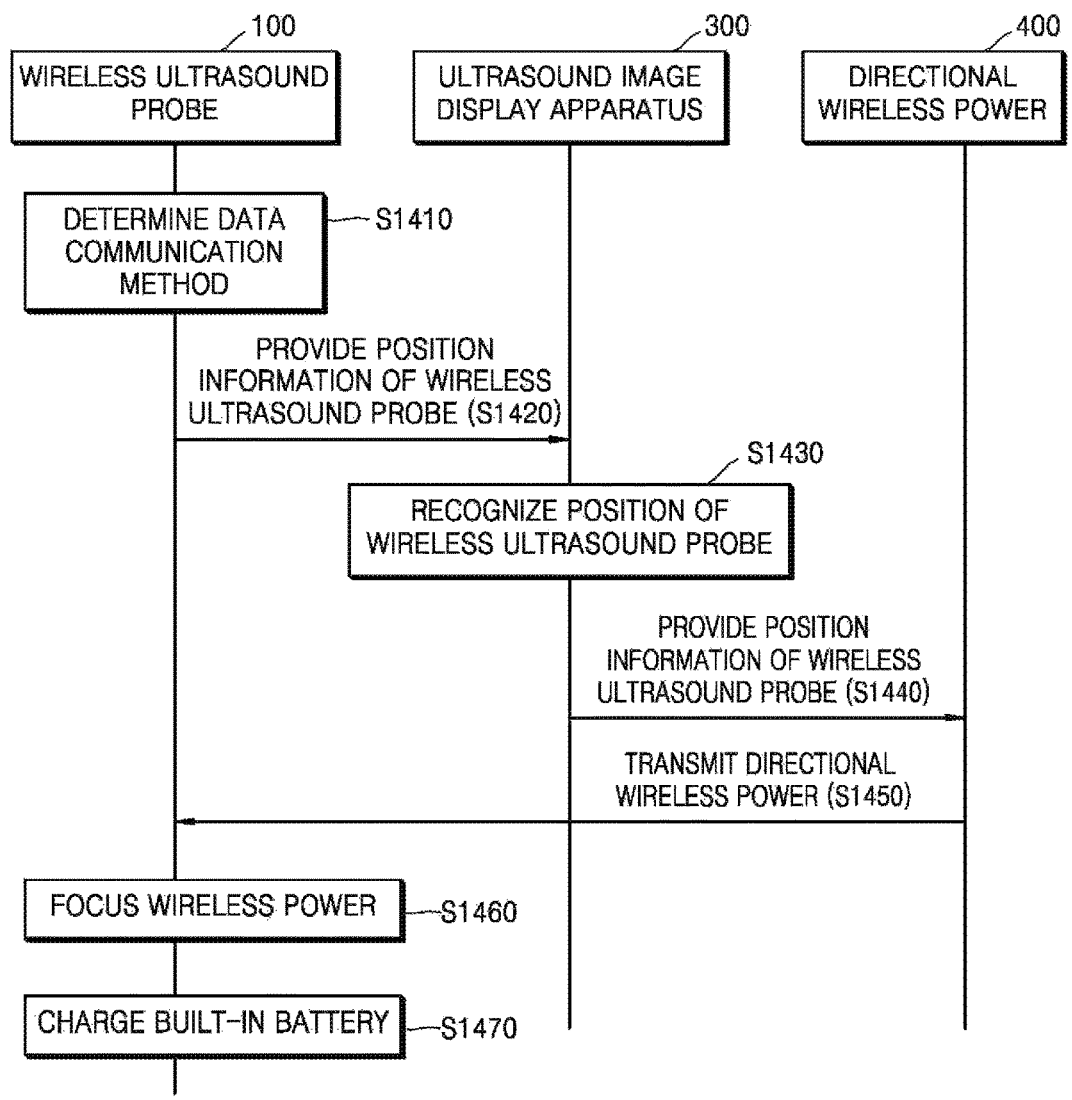
FIG. 14 is a flowchart of a method of charging a wireless ultrasound probe, according to an embodiment.

FIG. 14 is a flowchart of a method of charging the wireless ultrasound probe 100, according to an embodiment.

In Operation S1410, the wireless ultrasound probe 100 is wirelessly connected to the ultrasound image display apparatus 300 and determines a data communication method. In an embodiment, the wireless ultrasound probe 100 may select at least one of short-distance communication methods, for example, LAN, Wi-Fi, Bluetooth, Zigbee, WFD, UWB, IrDA, BLE, NFC, Wibro, WiMAX, SWAP, WiGig, and RF communications.

In Operation S1420, the wireless ultrasound probe 100 provides the information about the position of the wireless ultrasound probe 100 to the ultrasound image display apparatus 300. In an embodiment, the wireless ultrasound probe 100 may transmit the information about the position of the wireless ultrasound probe 100 to the ultrasound image display apparatus 300 by the data communication method determined in the operation S1410. In an embodiment, the wireless ultrasound probe 100 may transmit the position information to the ultrasound image display apparatus 300 by the 802.11n (802.11Ac) standard WIFI communication method capable of directional communication.

In Operation S1430, the ultrasound image display apparatus 300 identifies the position of the wireless ultrasound probe 100. In an embodiment, the ultrasound image display apparatus 300 may recognize the position of the wireless ultrasound probe 100, based on the position information transmitted by the wireless ultrasound probe 100 in the operation S1420.

In Operation S1440, the ultrasound image display apparatus 300 may provide the information about the position of the wireless ultrasound probe 100 to the directional wireless power unit 400.

In Operation S1450, the directional wireless power unit 400 transmits wireless power to the wireless ultrasound probe 100. In an embodiment, the directional wireless power unit 400 may directionally transmit wireless power toward the position of the wireless ultrasound probe 100, based on the information about the position of the wireless ultrasound probe 100 provided in the operation S1440.

In Operation S1460, the wireless ultrasound probe 100 focuses the wireless power transmitted by the directional wireless power unit 400. In Operation S1470, the wireless ultrasound probe 100 charges the battery 150.

Since the operations S1460 and S1470 are the same as the operations S760, and S770 described above with reference to FIG. 7, redundant descriptions thereof are omitted.

Figure 15:
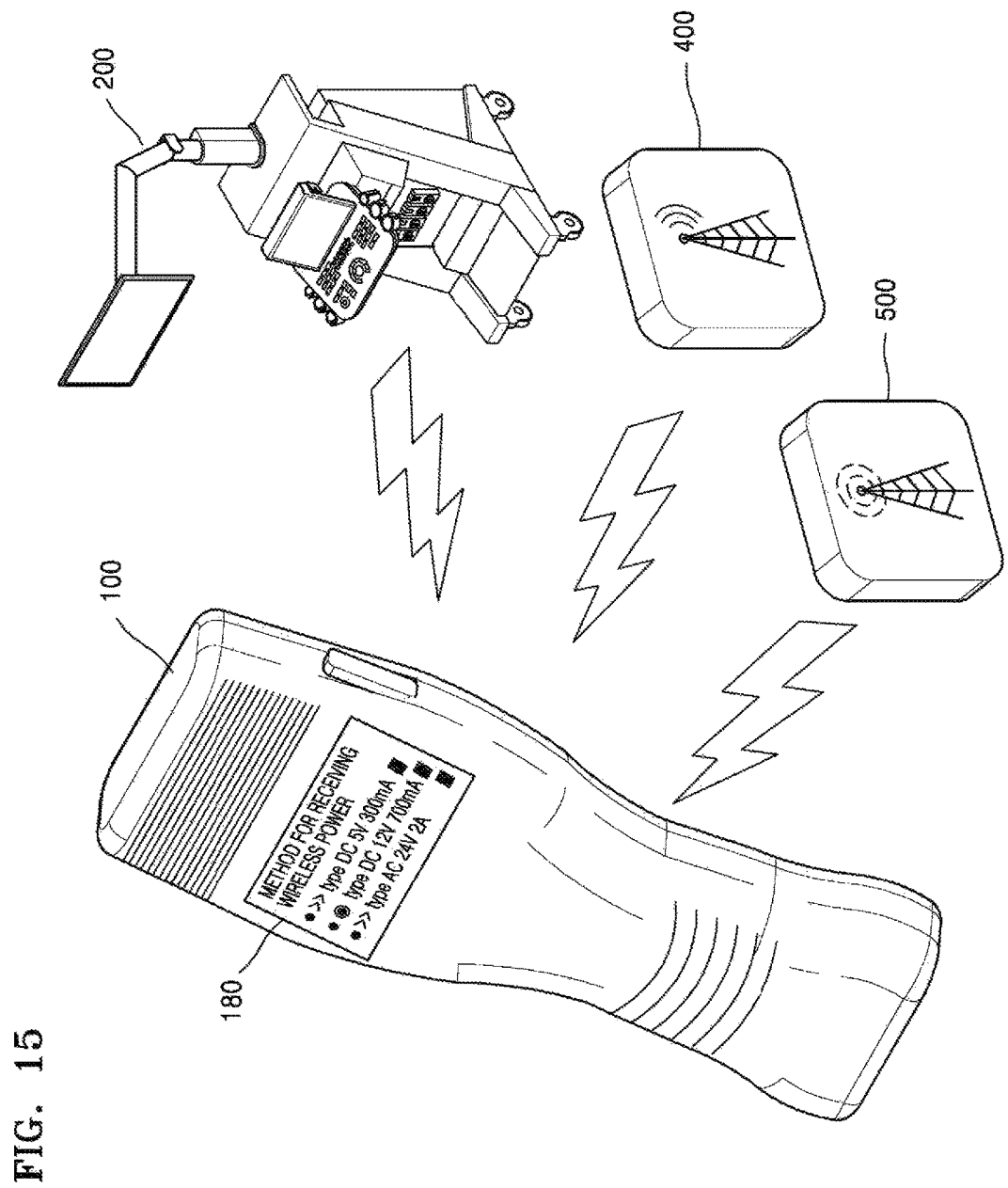
FIG. 15 is a conceptual view for explaining a method of displaying a wireless power transmission type, which is performed by a wireless ultrasound probe, according to an embodiment.

FIG. 15 is a conceptual view for explaining a method of displaying a wireless power transmission type, which is performed by the wireless ultrasound probe 100, according to an embodiment.

Referring to FIG. 15, the wireless ultrasound probe 100 may receive wireless power from any one of the ultrasound diagnosis apparatus 200, the directional wireless power unit 400, and an isotropic wireless power unit 500. Since the wireless ultrasound probe 100 and the ultrasound diagnosis apparatus 200 are the same as the wireless ultrasound probe 100 and the ultrasound diagnosis apparatus 200 described above with reference to FIGS. 1 and 2 and the directional wireless power unit 400 is the same as the directional wireless power unit 400 described above with reference to FIG. 13, redundant descriptions thereof are omitted.

The isotropic wireless power unit 500 may be a power unit for transmitting wireless power propagated in the form of a sphere regardless of directions from a point power source. The isotropic wireless power unit 500 may form a wireless power zone (Wi-Power) within a certain distance from the point power source.

The wireless ultrasound probe 100 may display a transmission type of wireless power provided by a plurality of wireless power supply sources to the wireless ultrasound probe 100. The wireless ultrasound probe 100 may include a display 180 for displaying the transmission type of wireless power received from the wireless power supply sources. In an embodiment, the display 180 may display the wireless power transmission type with at least one of text, an image, a color, and a combination thereof. In an embodiment, the wireless ultrasound probe 100 may further include a user input portion for receiving a user input to select any one of the wireless power transmission types displayed on the display 180. The wireless ultrasound probe 100 may receive wireless power through the wireless power transmission type selected based on the user input received from the user input portion.

Figure 16:
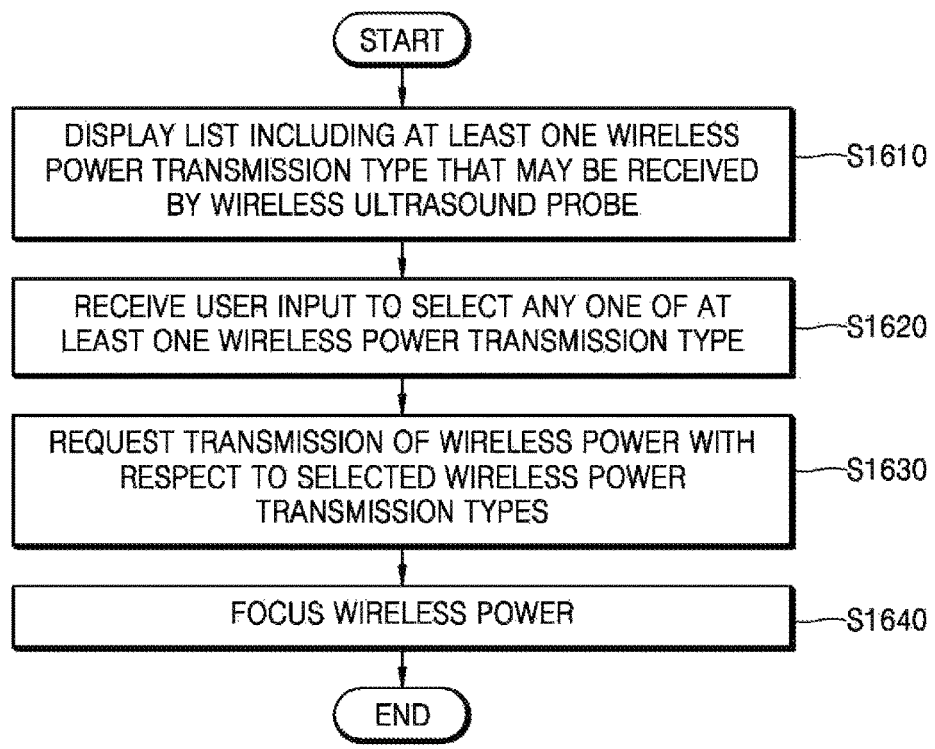
FIG. 16 is a flowchart of a method of displaying a wireless power transmission type, which is performed by a wireless ultrasound probe, according to an embodiment.

FIG. 16 is a flowchart of a method of displaying a wireless power transmission type, which is performed by the wireless ultrasound probe 100, according to an embodiment.

In Operation S1610, the wireless ultrasound probe 100 displays a list including at least one of wireless power transmission types for receiving wireless power. In an embodiment, the wireless ultrasound probe 100 may receive wireless power from the wireless power supply units, and may display a list of transmission types of wireless power received from the wireless power supply units. In an embodiment, the list displayed on the wireless ultrasound probe 100 may display wireless power transmission type with at least one of text, an image, a color, and a combination thereof.

In Operation S1620, the wireless ultrasound probe 100 receives a user input to select any one of at least one of the wireless power transmission types displayed in the list.

In Operation S1630, the wireless ultrasound probe 100 requests transmission of wireless power with respect to the selected wireless power transmission type based on the user input. In an embodiment, the wireless ultrasound probe 100 may transmit an electric signal requesting transmission of wireless power with respect to the wireless power supply unit that provides the wireless power transmission type selected by using the short-distance communication method. In an embodiment, the wireless ultrasound probe 100 may directionally receive wireless power when the wireless power supply unit selected according to the user input received in the operation S1620 is a directional wireless power unit. However, the present disclosure is not limited thereto, and the wireless ultrasound probe 100 may receive wireless power isotropically, for example, by a Wi-power method, when the wireless power supply unit selected according to the user input received in the operation S1620 is an isotropic wireless power unit.

In Operation S1640, the wireless ultrasound probe 100 focuses the wireless power that is provided. The wireless ultrasound probe 100 may charge the battery 150 by focusing the wireless power.

Figure 17:
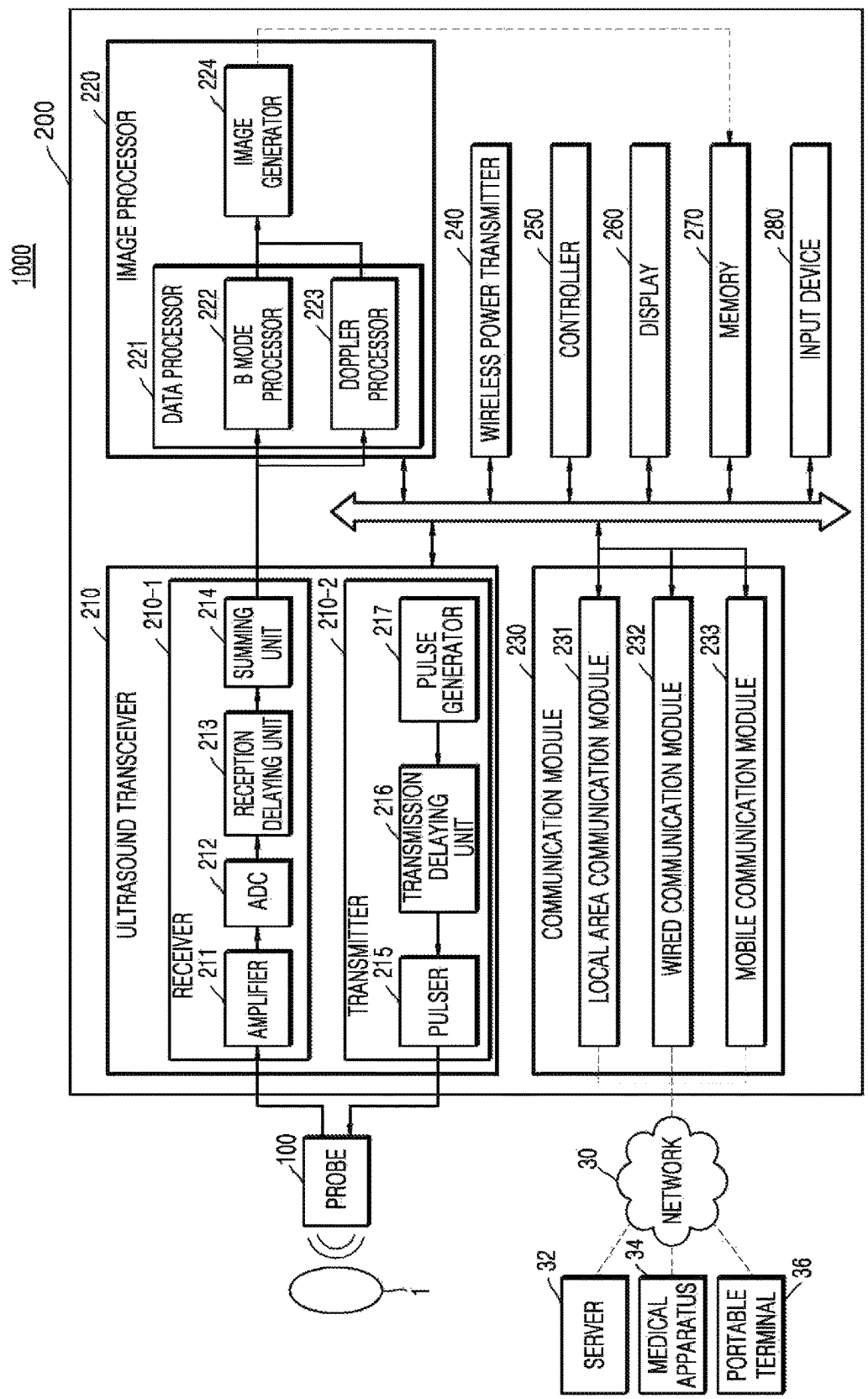
FIG. 17 is a block diagram illustrating a structure of an ultrasound system according to an embodiment.

FIG. 17 is a block diagram illustrating a structure of an ultrasound system 1000 according to an embodiment.

Referring to FIG. 17, the ultrasound system 1000 may include an ultrasound probe 100 for obtaining ultrasound image data by transmitting an ultrasound signal to an object 1 and receiving an echo signal reflected from the object 1, and the ultrasound diagnosis apparatus 200 wirelessly connected to the ultrasound probe 100 and transmitting wireless power to the ultrasound probe 100.

The ultrasound probe 100 transmits an ultrasound signal to the object 1 according to a driving signal applied by an ultrasound transceiver 210 and receives the echo signal reflected from the object 1. The ultrasound probe 100 includes a plurality of transducers and generates an ultrasound wave, that is, acoustic energy, while vibrating according to a received electric signal. Furthermore, the ultrasound probe 100 may be connected to a main body of the ultrasound diagnosis apparatus 200 in a wired or wireless manner. The ultrasound diagnosis apparatus 200 may include a plurality of ultrasound probes 100 according to the form of an embodiment. In an embodiment, the ultrasound probe 100 of FIG. 17 may be the same as the wireless ultrasound probe 100 described above with reference to FIGS. 1 and 2.

The ultrasound diagnosis apparatus 200 may include the ultrasound transceiver 210, an image processor 220, the communicator 230, the wireless power transmitter 240, the controller 250, a display 260, a memory 270, and an input device 280, which are connected to one another via a bus.

The ultrasound diagnosis apparatus 200 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

A transmitter 210-2 supplies a driving signal to the probe 100. The transmitter 110 includes a pulser 215, a transmission delaying unit 216, and a pulse generator 217. The pulse generator 217 generates pulses for forming transmission ultrasound waves based on a predetermined pulse repetition frequency (PRF), and the transmission delaying unit 216 delays the pulses by delay times necessary for determining transmission directionality. The pulses which have been delayed correspond to a plurality of piezoelectric vibrators included in the probe 100, respectively. The pulser 215 applies a driving signal (or a driving pulse) to the probe 100 based on timing corresponding to each of the pulses which have been delayed.

A receiver 210-1 generates ultrasound data by processing echo signals received from the probe 100. The receiver 120 may include an amplifier 211, an analog-to-digital converter (ADC) 212, a reception delaying unit 213, and a summing unit 214. The amplifier 211 amplifies echo signals in each channel, and the ADC 212 performs analog-to-digital conversion with respect to the amplified echo signals. The reception delaying unit 213 delays digital echo signals output by the ADC 124 by delay times necessary for determining reception directionality, and the summing unit 214 generates ultrasound data by summing the echo signals processed by the reception delaying unit 213. In some embodiments, the receiver 210-1 may not include the amplifier 211. In other words, if the sensitivity of the probe 100 or the capability of the ADC 212 to process bits is enhanced, the amplifier 211 may be omitted.

The image processor 220 generates an ultrasound image by scan-converting ultrasound data generated by the ultrasound transceiver 210. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B-mode processor 222 included in a data processor 221 extracts B mode components from ultrasound data and processes the B mode components. An image generator 224 may generate an ultrasound image indicating signal intensities as brightness based on the extracted B mode components 222.

Similarly, a Doppler processor 223 included in the data processor 221 may extract Doppler components from ultrasound data, and the image generator 224 may generate a Doppler image indicating a movement of an object as colors or waveforms based on the extracted Doppler components.

According to an embodiment, the image generator 224 may generate a three-dimensional (3D) ultrasound image via volume-rendering with respect to volume data and may also generate an elasticity image by imaging deformation of the object 1 due to pressure. Furthermore, the image generator 224 may display various pieces of additional information in an ultrasound image by using text and graphics. In addition, the generated ultrasound image may be stored in the memory 270.

The communication module 230 is connected to a network 30 by wire or wirelessly to communicate with an external device or a server. The communication module 230 may exchange data with a hospital server or another medical apparatus in a hospital, which is connected thereto via a PACS. Furthermore, the communication module 230 may perform data communication according to the digital imaging and communications in medicine (DICOM) standard.

The communication module 230 may transmit or receive data related to diagnosis of an object 1, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 230 may receive information about a diagnosis history or medical treatment schedule of a patient from a server and utilizes the received information to diagnose the patient. Furthermore, the communication module 230 may perform data communication not only with a server or a medical apparatus in a hospital, but also with a portable terminal of a medical doctor or patient.

The communication module 230 is connected to the network 30 by wire or wirelessly to exchange data with a server 32, a medical apparatus 34, or a portable terminal 36. The communication module 230 may include one or more components for communication with external devices. For example, the communicator 1300 may include a local area communication module 231, a wired communication module 232, and a mobile communication module 233.

The local area communication module 231 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 232 refers to a module for communication using electric signals or optical signals. Examples of wired communication techniques according to an embodiment may include communication via a twisted pair cable, a coaxial cable, an optical fiber cable, and an Ethernet cable.

The mobile communication module 233 transmits or receives wireless signals to or from at least one selected from a base station, an external terminal, and a server on a mobile communication network. The wireless signals may be voice call signals, video call signals, or various types of data for transmission and reception of text/multimedia messages.

The wireless power transmitter 240 may include phase array transducers that receive driving signals having different delay times and transform the driving signals into wireless power transmission signals. In an embodiment, the wireless power transmitter 240 may transmit wireless power by the magnetic resonance method. Since the wireless power transmitter 240 is the same as the wireless power transmitter 240 described above with reference to FIG. 6B, a redundant description thereof is omitted.

The controller 250 may control all operations of the ultrasound diagnosis apparatus 200. In other words, the controller 250 may control operations among the probe 100, the ultrasound transceiver 210, the image processor 220, the communication module 240, the display 260, the memory 270, and the input device 280 shown in FIG. 1.

In an embodiment, the controller 250 may adjust an order of driving signals so that the respective transducers may output wireless power in a particular order by applying delay times calculated with respect to the transducers. The controller 250 may control a focus direction and/or angle of wireless power by differently applying an order of driving signals to each of the transducers. In other words, the controller 250 may control the delay time of a driving signal by using the beamsteering technology and may set a focal position where beams including the wireless power are focused overlapping one another A display 260 displays the generated ultrasound image. The display 260 may display not only an ultrasound image, but also various pieces of information processed by the ultrasound diagnosis apparatus 200 on a screen image via a graphical user interface (GUI). In addition, the ultrasound diagnosis apparatus 200 may include two or more displays 260 according to embodiments.

The memory 270 stores various data processed by the ultrasound diagnosis apparatus 200. For example, the memory 270 may store medical data related to diagnosis of an object, such as ultrasound data and an ultrasound image that are input or output, and may also store algorithms or programs which are to be executed in the ultrasound diagnosis apparatus 200.

The memory 270 may be any of various storage media, e.g., a flash memory, a hard disk drive, EEPROM, etc. Furthermore, the ultrasound diagnosis apparatus 200 may utilize web storage or a cloud server that performs the storage function of the memory 270 online.

The input device 280 refers to a means via which a user inputs data for controlling the ultrasound diagnosis apparatus 200. The input device 280 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

In the present embodiment, the ultrasound probe 100 may determine a data communication method for transceiving ultrasound image data with the ultrasound diagnosis apparatus 200, recognized position information of the ultrasound probe 100 based on the determined data communication method, and provides the position information to the ultrasound diagnosis apparatus 200. The ultrasound diagnosis apparatus 200 may charge the battery 150 included in the ultrasound probe 100 by directionally transmitting wireless power based on the position information of the ultrasound probe 100.

Some or all of the ultrasound probe 100, the ultrasound transceiver 210, the image processor 220, the communicator 230, the wireless power transmitter 240, the controller 250, the display 260, the memory 270, and the input device 280 may be operated by a software module, but the present disclosure is not limited thereto and some of the above-described elements may be operated by hardware. Furthermore, at least one selected from the ultrasound transceiver 210, the image processor 220, and the communication module 230 may be included in the controller 250. However, embodiments of the present inventive concept are not limited thereto.

The embodiments of the present inventive concept may be written as computer programs and may be implemented in general-use digital computers that execute the programs using a non-transitory computer-readable recording medium.

Examples of the non-transitory computer-readable recording medium include magnetic storage media (e.g., ROM, floppy disks, hard disks, etc.), optical recording media (e.g., CD-ROMs, or DVDs), etc.

While one or more embodiments of the present inventive concept have been described with reference to the figures, it will be understood by those of ordinary skill in the art that various changes in form and details may be made therein without departing from the spirit and scope of the present inventive concept as defined by the following claims. Accordingly, the above embodiments and all aspects thereof are examples only and are not limiting.

What is claimed is:

1. A method of charging a wireless ultrasound probe wirelessly connected to an ultrasound diagnosis apparatus, the method comprising:
   selecting a wireless communication method, from among a plurality of wireless communication methods, for transmitting ultrasound image data of an object to the ultrasound diagnosis apparatus, based on a type of the ultrasound image data;
   tracking a position of the wireless ultrasound probe in real time;
   transmitting information of the tracked position of the wireless ultrasound probe to the ultrasound diagnosis apparatus via the selected wireless communication method; and
   charging a battery included in the wireless ultrasound probe by focusing wireless power directionally transmitted by the ultrasound diagnosis apparatus according to the information of the tracked position,
   wherein the selecting the wireless communication method comprises selecting a first wireless communication method for transmitting ultrasound raw data, or a second wireless communication method for transmitting an ultrasound image, from among the plurality of wireless communication methods.

2. The method of claim 1, wherein the selected wireless communication method is short-distance communication capable of tracking the position of the wireless ultrasound probe.

3. The method of claim 1, wherein the selected wireless communication method comprises at least one of short-distance data communication methods including 60 GHz millimeter wave (mmWave), wireless local area network (LAN), Wi-Fi, Bluetooth, Zigbee, Wi-Fi direct (WFD), ultra wideband (UWB), infrared data association (IrDA), Bluetooth low energy (BLE), near field communication (NFC), wireless broadband Internet (Wibro), world interoperability for microwave access (WiMAX), shared wireless access protocol (SWAP), wireless gigabit alliance (WiGig), and radio frequency (RF) communications.

4. The method of claim 1, wherein the transmitting of the information of the tracked position of the wireless ultrasound probe to the ultrasound diagnosis apparatus comprises determining any one of at least one short-distance communication method for transmitting the information of the position of the wireless ultrasound probe.

5. The method of claim 1, wherein the charging of the battery comprises charging the battery by focusing the wireless power transmitted by the ultrasound diagnosis apparatus by using a magnetic resonance method.

6. The method of claim 1, wherein the charging of the battery comprises charging the battery by focusing the wireless power transmitted by the ultrasound diagnosis apparatus by using a directional beamfocusing method.

7. The method of claim 1, further comprising transmitting raw data to the ultrasound diagnosis apparatus, the raw data being obtained by transmitting an ultrasound signal to the object and receiving an echo signal reflected from the object.

8. The method of claim 1, further comprising providing at least one of information about setting of the wireless ultrasound probe including information about identification of the wireless ultrasound probe, ultrasound preset setting information, information about a user of the wireless ultrasound probe, and information about the object, to the ultrasound diagnosis apparatus.

9. The method of claim 1, further comprising:
checking information about a state of the battery including a remaining amount of charge of the battery, a usage time of the battery, and a use state of the battery included in the wireless ultrasound probe; and
requesting transmission of wireless power from the ultrasound diagnosis apparatus based on the information about the state of the battery.

10. The method of claim 9, wherein the checking of the information about the state of the battery comprises providing an alarm signal to a user when the remaining amount of charge of the battery is less than a predetermined value.

11. The method of claim 9, wherein the requesting of the transmission of wireless power comprises requesting transmission of wireless power from the ultrasound diagnosis apparatus only when the wireless ultrasound probe is not in use.

12. The method of claim 1, further comprising displaying a transmission type of wireless power received from the ultrasound diagnosis apparatus.

13. The method of claim 1, further comprising:
dividing a capacity of the battery into a first battery capacity and a second battery capacity; and
primarily discharging the first battery capacity while the wireless ultrasound probe is in use.

14. The method of claim 1, wherein the tracking the position of the wireless ultrasound probe comprises:
updating the position of the wireless ultrasound probe according to a movement of a user using the wireless ultrasound probe.

15. A wireless ultrasound probe configured to wirelessly connect to an ultrasound diagnosis apparatus, the wireless ultrasound probe comprising:

an ultrasound transceiver configured to transmit an ultrasound signal to an object and receive an echo signal reflected from the object;
a communicator configured to transmit ultrasound image data obtained from the echo signal to the ultrasound diagnosis apparatus through a wireless communication method;
a controller configured to:
select a wireless communication method, from among a plurality of wireless communication methods, for transmitting the ultrasound image data to the ultrasound diagnosis apparatus, based on a type of the ultrasound image data,
track a position of the wireless ultrasound probe in real time, and
control the communicator to transmit information of the tracked position of the wireless ultrasound probe to the ultrasound diagnosis apparatus via the selected wireless communication method; and
a wireless power receiver configured to charge a battery included in the wireless ultrasound probe by absorbing wireless power directionally transmitted by the ultrasound diagnosis apparatus according to the information of the tracked position,
wherein the controller is further configured to select a first wireless communication method for transmitting ultrasound raw data, or a second wireless communication method for transmitting an ultrasound image, from among the plurality of wireless communication methods.

16. The wireless ultrasound probe of claim 15, wherein the controller controls the communicator to perform the selected wireless communication method with the ultrasound diagnosis apparatus by using short-distance communication to track a position of the wireless ultrasound probe.

17. The wireless ultrasound probe of claim 15, wherein the communicator uses at least one of short-distance data communication methods including 60 GHz millimeter wave (mmWave), wireless local area network (LAN), Wi-Fi, Bluetooth, Zigbee, Wi-Fi direct (WFD), ultra wideband (UWB), infrared data association (IrDA), Bluetooth low energy (BLE), near field communication (NFC), wireless broadband Internet (Wibro), world interoperability for microwave access (WiMAX), shared wireless access protocol (SWAP), wireless gigabit alliance (WiGig), and radio frequency (RF) communications, and
the controller tracks the position of the wireless ultrasound probe by using at least one of the short-distance data communication methods.

18. The wireless ultrasound probe of claim 15, wherein the controller selects a short-distance communication method for obtaining the information of the position of the wireless ultrasound probe.

19. The wireless ultrasound probe of claim 15, wherein the wireless power receiver charges the battery by absorbing the wireless power transmitted by the ultrasound diagnosis apparatus by a magnetic resonance method.

20. The wireless ultrasound probe of claim 15, wherein the wireless power receiver charges the battery by absorbing the wireless power transmitted by the ultrasound diagnosis apparatus by a directional beamfocusing method.

21. The wireless ultrasound probe of claim 15, wherein the communicator transmits raw data obtained from the echo signal to the ultrasound diagnosis apparatus.

22. The wireless ultrasound probe of claim 15, wherein the communicator transmits at least one of information about setting of the wireless ultrasound probe including information about identification of the wireless ultrasound probe, ultrasound preset setting information, information about a user of the wireless ultrasound probe, and information about the object, to the ultrasound diagnosis apparatus.

23. The wireless ultrasound probe of claim 15, wherein the controller checks information about a state of the battery including a remaining amount of charge of the battery, a usage time of the battery, and a use state of the battery, and requests transmission of wireless power from the ultrasound diagnosis apparatus based on the information about the state of the battery.

24. The wireless ultrasound probe of claim 23, further comprising an alarm display unit that provides an alarm signal to a user when the remaining amount of charge of the battery is less than a predetermined value.

25. The wireless ultrasound probe of claim 23, wherein the controller requests transmission of wireless power from the ultrasound diagnosis apparatus only when the wireless ultrasound probe is not in use.

26. The wireless ultrasound probe of claim 15, further comprising a display that displays a transmission type of wireless power received from the ultrasound diagnosis apparatus.

27. The wireless ultrasound probe of claim 15, wherein the controller divides a capacity of the battery into a first battery capacity and a second battery capacity and primarily discharges the first battery capacity while the wireless ultrasound probe is in use.

28. The wireless ultrasound probe of claim 15, wherein the controller is further configured to update the position of the wireless ultrasound probe according to a movement of a user using the wireless ultrasound probe.

29. An ultrasound system comprising:
   an ultrasound probe configured to obtain ultrasound image data by transmitting an ultrasound signal to an object and receiving an echo signal reflected from the object; and
   an ultrasound diagnosis apparatus configured to wirelessly connect to the ultrasound probe and wirelessly transmit power to the ultrasound probe,
   wherein the ultrasound probe is configured to:
      select a wireless communication method, from among a plurality of wireless communication methods, for wirelessly transmitting the obtained ultrasound image data, based on a type of the ultrasound image data,
      track a position of the ultrasound probe in real time, and
      transmit information of the tracked position of the ultrasound probe to the ultrasound diagnosis apparatus via the selected wireless communication method, and
   the ultrasound diagnosis apparatus is configured to charge a battery included in the ultrasound probe by directionally transmitting wireless power to the ultrasound probe based on the information of the tracked position of the ultrasound probe,
   wherein the ultrasound probe is further configured to select a first wireless communication method for transmitting ultrasound raw data, or a second wireless communication method for transmitting an ultrasound image, from among the plurality of wireless communication methods.

30. The ultrasound system of claim 29, wherein the ultrasound diagnosis apparatus comprises a wireless power transmitter that directionally transmits the wireless power toward the position of the ultrasound probe by controlling a delay time of a wireless power signal in a particular order.

31. The ultrasound system of claim 30, wherein the ultrasound diagnosis apparatus further comprises a direction controller that is connected to the wireless power transmitter and changes a transmission direction of the wireless power transmitter to at least one of a first direction, a second direction perpendicular to the first direction, and a third direction perpendicular to each of the first direction and the second direction.

32. The ultrasound system of claim 31, wherein the direction controller rotates the transmission direction of the wireless power transmitter to at least one of the first direction, the second direction, and the third direction.

33. The ultrasound system of claim 29, wherein the ultrasound probe is further configured to update the position of the ultrasound probe according to a movement of a user using the ultrasound probe.

34. A non-transitory computer readable recording medium having recorded thereon a program, which when executed by a computer, performs the method of claim 1.

* * * * *